United States Patent
Ku et al.

(10) Patent No.: US 12,398,205 B2
(45) Date of Patent: *Aug. 26, 2025

(54) ANTI-INTERFERON GAMMA ANTIBODIES AND USES THEREOF

(71) Applicant: Elixiron Immunotherapeutics (Hong Kong) Limited, Central Hong Kong (CN)

(72) Inventors: Cheng-Lun Ku, Taoyuan (TW); Han-Po Shih, Taoyuan (TW); Chia-Hao Lin, New Taipei (TW); Jing-Ya Ding, Taoyuan (TW); Jing-Yi Huang, Taipei (TW); Yi-Ting Kuo, Taichung (TW)

(73) Assignee: Elixiron Immunotherapeutics (Hong Kong) Limited, Central Hong Kong (CN)

( * ) Notice: Subject to any disclaimer, the term of this patent is extended or adjusted under 35 U.S.C. 154(b) by 943 days.

This patent is subject to a terminal disclaimer.

(21) Appl. No.: 17/175,086

(22) Filed: Feb. 12, 2021

(65) Prior Publication Data

US 2021/0171625 A1 Jun. 10, 2021

Related U.S. Application Data

(63) Continuation of application No. 16/331,935, filed as application No. PCT/CN2018/085836 on May 7, 2018, now Pat. No. 10,968,274.

(60) Provisional application No. 62/501,952, filed on May 5, 2017.

(51) Int. Cl.
*C07K 16/24* (2006.01)

(52) U.S. Cl.
CPC ........ *C07K 16/249* (2013.01); *C07K 2317/41* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 6,171,586 | B1 | 1/2001 | Lam et al. |
| 6,267,958 | B1 | 7/2001 | Andya et al. |
| 7,335,743 | B2 | 2/2008 | Welcher et al. |
| 10,813,974 | B2 | 10/2020 | Chen et al. |
| 10,968,274 | B2 | 4/2021 | Ku et al. |
| 2005/0260186 | A1 | 11/2005 | Bookbinder et al. |
| 2006/0104968 | A1 | 5/2006 | Bookbinder et al. |
| 2011/0311550 | A1 | 12/2011 | Law et al. |
| 2014/0004127 | A1 | 1/2014 | Welcher et al. |

FOREIGN PATENT DOCUMENTS

| | | |
|---|---|---|
| CN | 104159919 A | 11/2014 |
| WO | 2006044908 A2 | 4/2006 |
| WO | 2006109191 A2 | 10/2006 |
| WO | 2013078378 A1 | 5/2013 |

OTHER PUBLICATIONS

Rudikoff et al. Proc. Natl. Acad. Sci. 1982. 79: 1979-1983 (Year: 1982).*
Bedouelle et al. FEES J. Jan. 2006;273(1):34-46 (Year: 2006).*
Vajdos et al. J Mol Biol. Jul. 5, 2002;320(2):415-28 (Year: 2002).*
Saputri et al. mSystems. 2023. 8(6):e0072223 (Year: 2023).*
Sam-Yellowe. Immunology: Overview and laboratory manual (1st ed). 2021. Springer Nature Switzerland (Year: 2021).*
Klein et al. Cell. 2013. 153:126-138 (Year: 2013).*
International Search Report and Written Opinion in International Patent Application No. PCT/CN18/085836, dated Aug. 16, 2018, in 14 pages.
Edvardsen, Kine, et al. "Peripheral blood cells from patients with autoimmune Addison's disease poorly respond to Interferons in vitro, despite elevated serum levels of interferon-inducible Chemokines." Journal of Interferon & Cytokine Research 35.10 (2015): 759-770.
Bisping, G., et al. "Patients with inflammatory bowel disease (IBD) reveal increased induction capacity of intracellular interferon-gamma (IFN-γ) in peripheral CD8+ lymphocytes co-cultured with intestinal epithelial cells." Clinical & Experimental Immunology 123.1 (2001): 15-22.
Benci, Joseph L., et al. "Tumor interferon signaling regulates a multigenic resistance program to immune checkpoint plockade." Cell 167.6 (2016): 1540-1554.
Lefranc, Marie-Paule. "IMGT, the international ImMunoGeneTics database." Nucleic Acids Research 29.1 (2001): 207-209.
Chothia, Cyrus, and Arthur M. Lesk. "Canonical structures for the hypervariable regions of immunoglobulins." Journal of Molecular Biology 196.4 (1987): 901-917.
Lefranc, Marie-Paule. "Unique database numberings system for immunogenetic analysis." Immunology Today 18.11 (1997): 509.
Lefranc, M. P. "The IMGT unique numbering for immunoglobulins, T-cell receptors, and Ig-like domains." The Immunologist 7.4 (1999): 132-136.
Lefranc, Marie-Paule, et al. "IMGT unique numbering for immunoglobulin and T cell receptor variable domains and Ig superfamily V-like domains." Developmental & Comparative Immunology 27.1 (2003): 55-77.
Ruiz, Manuel, and Marie-Paule Lefranc. "IMGT gene identification and Colliers de Perles of human immunoglobulins with known 3D structures." Immunogenetics 53.10-11 (2002): 857-883.
Kaas, Quentin, and Marie-Paule Lefranc. "IMGT Colliers de Perles: standardized sequence-structure representations of the IgSF and MhcSF superfamily domains." Current Bioinformatics 2.1 (2007): 21-30.

(Continued)

*Primary Examiner* — Anne M. Gussow
*Assistant Examiner* — Brianna K Swartwout
(74) *Attorney, Agent, or Firm* — DUANE MORRIS LLP

(57) ABSTRACT

Provided is an anti-INF-γ antibody. Also provided are a composition comprising the antibody and a pharmaceutical application of the antibody in treating IFN-γ mediated syndrome.

14 Claims, 9 Drawing Sheets

Specification includes a Sequence Listing.

(56) References Cited

OTHER PUBLICATIONS

Kaas, Quentin, Manuel Ruiz, and Marie-Paule Lefranc. "IMGT/3Dstructure-DB and IMGT/StructuralQuery, a database and a tool for immunoglobulin, T cell receptor and MHC structural data." Nucleic Acids Research 32.suppl_1 (2004): D208-D210.

Partial Supplementary European Search Report and Provisional Opinion in EP Patent Application No. 18794042.4, dated Dec. 4, 2020, in 14 pages.

Dondelinger, Mathieu, et al. "Understanding the significance and implications of antibody numbering and antigen-binding surface/residue definition." Frontiers in Immunology 9 (2018): 2278, pp. 1-15.

Definition: Vector.Biology online. https://www.biologyonline.com/dictionary/vector. accessed Feb. 20, 2024, 2 pages. (Year: 2024).

Definition: Vectors 101. American Society of Gene + Cell Therapy: https://patienteducation.asgct.org/gene-therapy-101/vectors-101. accessed Feb. 20, 2024, 1 page. (Year: 2024).

Lee, Seung-Jin, et al. "Interferon regulatory factor-1 is prerequisite to the constitutive expression and IFN-γ-induced upregulation of B7-H1 (CD274)." FEBS Letters 580.3 (2006): 755-762.

Sela-Culang, Inbal, Vered Kunik, and Yanay Ofran. "The structural basis of antibody-antigen recognition." Frontiers in Immunology 4 (2013): 302, 13 pages.

* cited by examiner

ANTI-INTERFERON GAMMA ANTIBODIES AND USES THEREOF

RELATED APPLICATIONS

The present application is a continuation of and claims priority to U.S. patent application Ser. No. 16/331,935, filed Mar. 8, 2019 now patented as U.S. Pat. No. 10,968,274, which is a National Stage Entry of International Patent Application No. PCT/CN2018/085836, filed May 7, 2018, which claims priority to U.S. Provisional Patent Application No. 62/501,952, filed May 5, 2017, the contents each of which are herein incorporated by reference in their entirety.

TECHNICAL FIELD

The present disclosure relates to novel recombinant antibodies or any antigen-binding fragments thereof directed against interferon gamma (IFN-γ). The present disclosure also relates to the uses of said antibodies or any antigen-binding fragments thereof in the amelioration, treatment or prevention of IFN-γ-mediated disease.

DESCRIPTION OF RELATED ART

Interferon gamma (IFN-γ) is a cytokine that plays a critical role in both innate and adaptive immunity. It is known in the art that IFN-γ is related to inflammation and autoinflammationatory diseases. For instance, Kine Edvardsen et al. disclosed that autoreactive 21 OH-specific T cells producing large amounts of IFN-γ are also prevalent in Addison's disease patients (J Interferon Cytokine Res. 2015 Oct. 1; 35(10): 759-770). Bisping G et al concluded that patients with inflammatory bowel disease, even in an inactive state of disease, exert an increased capacity for IFN-γ induction in CD8+ lymphocytes mediated by intestinal epithelial cells (Clin Exp Immunol. 2001 January; 123(1): 15-22.).

In contrast to the aforesaid pro-inflammatory function, in certain settings, IFN-γ expression could lead to suppressed T-cell activities. For example, Benci J L et al showed that tumor IFN-γ signaling could regulate a multigenic resistance program to immune checkpoint blockade (Cell, 2016, December 167:1540-1554). Their data indicated blocking or neutralizing IFN-γ could improve function of distinctive exhausted T cell subsets. Therefore, neutralizing anti-IFN-γ agents could also be used to enhance T-cell immunity.

In light of the potential pharmaceutical applications of anti-IFN-γ agents for the treatment of inflammation related diseases, there is a continued need for anti-IFN-γ antibodies useful for industrial and pharmaceutical application.

SUMMARY

One of the objectives of the present disclosure is to provide a novel anti-IFN-γ antibody and composition comprising the same for neutralizing interferon-γ mediated activity. Another objective of the present disclosure is to provide a pharmaceutical composition comprising said anti-IFN-γ antibody for treating IFN-γ mediated syndrome.

In order to accomplish the aforesaid objectives, the present disclosure provides an isolated antibody comprising: $V_H$ CDR1 comprising an amino acid sequence selected from SEQ ID NO: 120, 123, 126, 129, 144, 147, 150, or 153; $V_H$ CDR2 comprising an amino acid sequence selected from SEQ ID NO: 121, 124, 127, 130, 145, 148, 151, or 154; $V_H$ CDR3 comprising an amino acid sequence selected from SEQ ID NO: 122, 125, 128, 131, 146, 149, 152, or 155; $V_L$ CDR1 comprising an amino acid sequence selected from SEQ ID NO: 132, 135, 138, 141, 156, 158, 160, or 162; $V_L$ CDR2 comprising an amino acid sequence selected from SEQ ID NO: 133, 136, 139, 142, 157, 159, 161, or 163; and $V_L$ CDR3 comprising an amino acid sequence selected from SEQ ID NO: 134, 137, 140, or 143.

The present disclosure also provides an isolated antibody that specifically binds to the same epitope as the aforesaid antibody. In some embodiments, the aforesaid antibody further comprises the epitope binding characteristics as described below and elsewhere herein.

The present disclosure then provides an isolated antibody, wherein the antibody specifically binds to one or more amino acid residues within amino acids 30-52 or 36-48 and amino acids 78-92 or 82-92 of human IFN-γ, wherein said amino acids 30-52 comprises amino acids of SEQ ID NO: 167, said amino acids 36-48 comprises amino acids of SEQ ID NO: 171, said 78-92 comprises amino acids of SEQ ID NO: 168, and said 82-92 comprises amino acids of SEQ ID NO: 172.

The present disclosure more provides an isolated antibody, wherein the antibody specifically binds to one or more amino acid residues within amino acids 36-48 and 82-92 of human IFN-γ, wherein said amino acids 36-48 comprises amino acids of SEQ ID NO: 171, and said amino acids of 82-92 comprises amino acid SEQ ID NO: 172.

The present disclosure also provides an isolated antibody that specifically binds to an epitope of human IFN-γ, wherein said epitope comprises K43, Q48, and K86 of human IFN-γ; wherein said human IFN-γ comprises SEQ ID NO: 166.

The present disclosure then provides an isolated polynucleotide that encodes the aforesaid isolated antibody. In some embodiments, the isolated polynucleotide encodes an antibody, wherein the antibody comprises a $V_H$ CDR1 comprising an amino acid sequence selected from SEQ ID NO: 120, 123, 126, 129, 144, 147, 150, or 153; $V_H$ CDR2 comprising an amino acid sequence selected from SEQ ID NO: 121, 124, 127, 130, 145, 148, 151, or 154; $V_H$ CDR3 comprising an amino acid sequence selected from SEQ ID NO: 122, 125, 128, 131, 146, 149, 152, or 155; $V_L$ CDR1 comprising an amino acid sequence selected from SEQ ID NO: 132, 135, 138, 141, 156, 158, 160, or 162; $V_L$ CDR2 comprising an amino acid sequence selected from SEQ ID NO: 133, 136, 139, 142, 157, 159, 161, or 163; and $V_L$ CDR3 comprising an amino acid sequence selected from SEQ ID NO: 134, 137, 140, or 143.

In some embodiments, the isolated polynucleotide comprises a first sequence having at least 90% identity to SEQ ID NO: 173, 175, 176, 177, 179, or 181, encoding $V_H$ of the antibody and a second sequence having at least 90% identity to SEQ ID NO: 174, 178, 180, or 182, encoding $V_L$ of the antibody.

The present disclosure also provides a vector comprising the aforesaid polynucleotide.

The present disclosure also provides an isolated host cell comprising the aforesaid vector.

The present disclosure then provides an isolated host cell expressing the aforesaid isolated antibody.

The present disclosure also provides a composition for neutralizing interferon-γ activity, comprising: the aforesaid isolated antibody; and a carrier.

The present disclosure then provides a composition for treating an IFN-γ mediated syndrome, comprising: an effective amount of the aforesaid isolated antibody; and a pharmaceutically acceptable carrier.

The present disclosure more provides a method for treating an IFN-γ mediated syndrome, comprising: administering a subject in need an effective amount of an isolated antibody.

The present disclosure also provides a method for detecting interferon-γ in an environment, comprising: (A) applying the aforesaid isolated antibody into said environment; (B) incubating said environment with an anti-IgG antibody; wherein said anti-IgG antibody is conjugated with a detectable label; and (C) detecting said detectable label.

DETAILED DESCRIPTION

Figure 1:
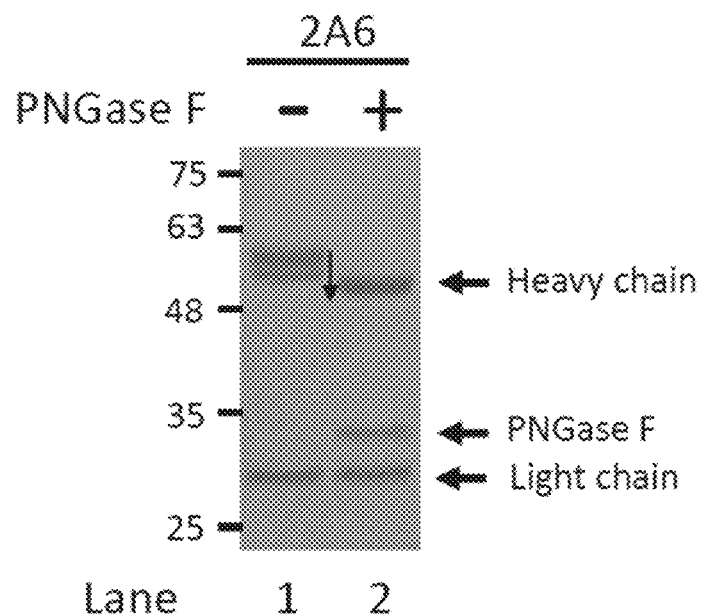
FIG. 1 shows the result of the PNGase F digestion assay of antibody 2A6 in Example 1. "−" represents untreated group; "+" represents the group treated with PNGase F. The arrow indicates the shift of band after PNGase F treatment.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example, "1 to 50," includes "2 to 25," "5 to 20," "25 to 50," "1 to 10," etc.

All publications, patents, patent applications, and other documents referenced in this disclosure are hereby incorporated by reference in their entireties for all purposes to the same extent as if each individual publication, patent, patent application or other document were individually indicated to be incorporated by reference herein for all purposes.

It is to be understood that both the foregoing general description, including the drawings, and the following detailed description are exemplary and explanatory only and are not restrictive of this disclosure.

The technical and scientific terms used in the descriptions herein will have the meanings commonly understood by one of ordinary skill in the art, unless specifically defined otherwise.

The term "antibody" as referred to herein includes intact antibodies and any antigen-binding fragment (i.e., "antigen-binding portion") or single chains thereof. An "antibody" refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each of $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The extent of the framework regions and CDRs has been defined according to Kabat et al. (see, Kabat et al., Sequences of Proteins of Immunological Interest, U.S. Department of Health and Human Services, 1991) and the ImMunoGeneTics database (IMGT) (see, Lefranc, Nucleic Acids Res 29:207-9, 2001; and online at imgt.cines.fr/IMGT_vquest/vquest?livret=0&Option=humanIg).

The "Kabat system" means in the context of the present disclosure the standard for numbering the residues in a consistent manner according to Kabat (1991; Sequences of Proteins of Immunological Interest, 5th edit., NIH publication no. 91-3242U.S. Department of Health and Human services) and Chothia (1987; J. Mol. Biol. 196, 901-917). This numbering system is widely used by the skilled artisans and is based on sequence variability and three dimensional loops of the variable domain region which are important in antigen-binding activity. All the residues of the light chains or heavy chains have distinct positions in the Kabat system; i.e. the Kabat system applies to CDRs as well as to framework regions. The positions of specific residues of any antibody may be numbered according to the Kabat system. The rules to identify the CDR regions of $V_H$ and $V_L$ chains according to Kabat system are shown in www.bioinf.org.uk/abs.

The IMGT unique numbering system is an alternative to the Kabat System that allows one to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering system, the conserved amino acids always have the same position, for instance cysteine 23 (1st-CYS), tryptophan 41 (CONSERVED-TRP), hydrophobic amino acid 89, cysteine 104 (2nd-CYS), phenylalanine or tryptophan 118 (J-PHE or J-TRP). The IMGT unique numbering system provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering system is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

The term "antigen-binding fragment" as used herein refers to an antibody fragment, such as for example, a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, or any other antibody fragment that binds to an antigen but does not comprise a complete or intact antibody structure. An antigen-binding fragment is capable of binding to the same antigen to which the parent antibody or a parent antibody fragment (e.g., a parent scFv) binds. In certain embodiments, an antigen-binding fragment may comprise one or more CDRs from a particular human antibody grafted to a framework region from one or more different human antibodies.

Among the above antigen-binding fragments, a Fab, which is a structure having the light chain and heavy chain variable regions, the light chain constant region, the heavy chain first constant region (CH1), and has one antigen-binding site. A Fab' differs from the Fab in that the Fab' has a hinge region including at least one cysteine residue at the C-terminal of the heavy chain CH1 domain. A F(ab')$_2$ is produced when cysteine residues at the hinge region of Fab' are joined by a disulfide bond.

An Fv is a minimal antibody fragment, having only heavy chain variable region and light chain variable regions. A recombinant technique for producing the Fv fragment is well known in the art. "Single-chain Fv antibody" or "scFv" refers to an engineered antibody consisting of a light chain variable region and a heavy chain variable region connected to one another directly or via a peptide linker sequence. A two-chain Fv may have a structure in which heavy chain variable regions are linked to light chain variable regions by a non-covalent bond. A single-chain Fv may generally form a dimer structure as in the two-chain Fv, wherein heavy chain variable regions are covalently bound to light chain variable regions via a peptide linker or the heavy and light chain variable regions are directly linked to each other at the C-terminals thereof. The linker may be a peptide linker including any 1 to 100 or 2 to 50 amino acids, and proper sequences useful therefor are well known in the art.

The antigen-binding fragment may be obtained using a protease (for example, a whole antibody can be digested with papain to obtain Fab fragments, or can be digested with pepsin to obtain F(ab')2 fragments), or may be prepared by a genetic recombinant technique.

An "isolated antibody," as used herein, is intended to refer to an antibody that is substantially free of other antibodies having different antigenic specificities (e.g., an isolated antibody that specifically binds IFN-γ is substantially free of antibodies that specifically bind antigens other than IFN-γ). An isolated antibody that specifically binds IFN-γ may, however, have cross-reactivity to other antigens, such as IFN-γ molecules from other species. Moreover, an isolated antibody may be substantially free of other cellular material and/or chemicals.

The terms "monoclonal antibody" or "monoclonal antibody composition" as used herein refer to a preparation of antibody molecules of homogeneous molecular composition. A monoclonal antibody composition displays a single binding specificity and affinity for a particular epitope.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences.

The term "recombinant human antibody," as used herein, includes all human antibodies that are prepared, expressed, created or isolated by recombinant means, such as (a)

antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant human antibodies are sequences that, while derived from and related to human germline $V_H$ and $V_L$ sequences, may not naturally exist within the human antibody germline repertoire in vivo.

The term "humanized antibody" is referred to as an antibody that is generated from non-human species and comprises protein sequences that have been modified to increase their similarity to antibody variants produced naturally in humans. The humanization process could be necessary to avoid undesired immunogenic effect when applying a non-human source antibody in human. In comparison, the term "chimeric antibody" as referred to herein is an antibody made by fusing the antigen binding region (i.e. $V_H$ and $V_L$) from one species with the constant domain with another.

The term "$K_{assoc}$" or "$K_a$," as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art.

As used herein, an "epitope" is referred as a portion of an antigen recognized and bound by a specific antibody, which determines the antigenic specificity of the antigen. Epitope is also known as an antigenic determinant Specifically, in the present disclosure, the epitope could be a specific domain or a combination of domains of human IFN-γ. In some embodiments of the present disclosure, the specific domains or combination of domains are of the human IFN-γ that comprises the amino acid sequence of SEQ ID NO: 166

In one embodiment of the present disclosure, IFN-γ comprises SEQ ID NO: 166, and the antibody of the present disclosure specifically binds to one or more amino acid residues within amino acids 30-52 or 36-48 of SEQ ID NO: 166 and amino acids 78-92 or 82-92 of SEQ ID NO: 166. In a specific embodiment of the present disclosure, the antibody of the present disclosure specifically binds to IFN-γ at amino acids 30-52 and amino acids 78-92 of SEQ ID NO: 166. In this particular embodiment, said amino acids 30-52 and amino acids 78-92 of SEQ ID NO: 166 form the epitope of the antibody of the present disclosure. In another embodiment, the antibody of the present disclosure specifically binds to IFN-γ at amino acids 36-48 and amino acids 82-92 of SEQ ID NO: 166. In this particular embodiment, said amino acids 36-48 and amino acids 82-92 of SEQ ID NO: 166 form the epitope of the antibody of the present disclosure.

As used herein, an antibody that "specifically binds to IFN-γ" is intended to refer to an antibody that binds to IFN-γ with a binding value $K_D$ of less than $1\times10^{-8}$ M, less than $1\times10^{-9}$ M, less than $1\times10^{-10}$ M, less than $1\times10^{-11}$ M, or even less.

The First Aspect of the Present Disclosure.

In the first aspect of the present disclosure, an isolated antibody or any antigen-binding portion is provided. Said isolated antibody or any antigen-binding portion comprises:
  (a). $V_H$ CDR1 comprising an amino acid sequence selected from SEQ ID NO: 120, 123, 126, 129, 144, 147, 150, or 153;
  (b). $V_H$ CDR2 comprising an amino acid sequence selected from SEQ ID NO: 121, 124, 127, 130, 145, 148, 151, or 154;
  (c). $V_H$ CDR3 comprising an amino acid sequence selected from SEQ ID NO: 122, 125, 128, 131, 146, 149, 152, or 155;
  (d). $V_L$ CDR1 comprising an amino acid sequence selected from SEQ ID NO: 132, 135, 138, 141, 156, 158, 160, or 162;
  (e). $V_L$ CDR2 comprising an amino acid sequence selected from SEQ ID NO: 133, 136, 139, 142, 157, 159, 161, or 163; and
  (f). $V_L$ CDR3 comprising an amino acid sequence selected from SEQ ID NO: 134, 137, 140, or 143.

In a specific embodiment, an antibody 2A6 is provided. Said $V_H$ CDR1, $V_H$ CDR2, and $V_H$ CDR3 of said antibody 2A6 comprise amino acid sequences of SEQ ID NO: 120, SEQ ID NO: 121, and SEQ ID NO: 122 respectively; and said $V_L$ CDR1, $V_L$ CDR2, and $V_L$ CDR3 of said antibody 2A6 comprise amino acid sequences of SEQ ID NO: 132, SEQ ID NO: 133, and SEQ ID NO: 134, respectively. Alternatively, said $V_H$ CDR1, $V_H$ CDR2, and $V_H$ CDR3 of said antibody 2A6 comprise amino acid sequences of SEQ ID NO: 144, SEQ ID NO: 145, and SEQ ID NO: 146 respectively; wherein said $V_L$ CDR1, $V_L$ CDR2, $V_L$ CDR3 of said antibody 2A6 comprise amino acid sequences of SEQ ID NO: 156, SEQ ID NO: 157, and SEQ ID NO: 134 respectively.

In a specific embodiment, an antibody 2B6 is provided. Said $V_H$ CDR1, $V_H$ CDR2, and $V_H$ CDR3 of said antibody 2B6 comprise amino acid sequences of SEQ ID NO: 123, SEQ ID NO: 124, and SEQ ID NO: 125 respectively; wherein said $V_L$ CDR1, $V_L$ CDR2, $V_L$ CDR3 of said antibody 2B6 comprise amino acid sequences of SEQ ID NO: 135, SEQ ID NO: 136, and SEQ ID NO: 137 respectively. Alternatively, said $V_H$ CDR1, $V_H$ CDR2, and $V_H$ CDR3 of said antibody 2B6 comprise amino acid sequences of SEQ ID NO: 147, SEQ ID NO: 148, and SEQ ID NO: 149 respectively; wherein said $V_L$ CDR1, $V_L$ CDR2, $V_L$ CDR3 of said antibody 2B6 comprise amino acid sequences of SEQ ID NO: 158, SEQ ID NO: 159, and SEQ ID NO: 137 respectively.

In a specific embodiment, an antibody 1E8 is provided. Said $V_H$ CDR1, $V_H$ CDR2, and $V_H$ CDR3 of said antibody 1E8 comprise amino acid sequences of SEQ ID NO: 126, SEQ ID NO: 127, and SEQ ID NO: 128 respectively; wherein said $V_L$ CDR1, $V_L$ CDR2, $V_L$ CDR3 of said antibody 1E8 comprise amino acid sequences of SEQ ID NO: 138, SEQ ID NO: 139, and SEQ ID NO: 140 respectively. Alternatively, said $V_H$ CDR1, $V_H$ CDR2, and $V_H$ CDR3 of said antibody 1E8 comprise amino acid sequences of SEQ ID NO: 150, SEQ ID NO: 151, and SEQ ID NO: 152 respectively; wherein said $V_L$ CDR1, $V_L$ CDR2, $V_L$ CDR3 of said antibody 1E8 comprise amino acid sequences of SEQ ID NO: 160, SEQ ID NO: 161, and SEQ ID NO: 140 respectively.

In a specific embodiment, an antibody 2F2 is provided. Said $V_H$ CDR1, $V_H$ CDR2, and $V_H$ CDR3 of said antibody 2F2 comprise amino acid sequences of SEQ ID NO: 129, SEQ ID NO: 130, and SEQ ID NO: 131 respectively; wherein said $V_L$ CDR1, $V_L$ CDR2, $V_L$ CDR3 of said antibody 2F2 comprise amino acid sequences of SEQ ID NO: 141, SEQ ID NO: 142, and SEQ ID NO: 143 respectively. Alternatively, said $V_H$ CDR1, $V_H$ CDR2, and $V_H$ CDR3 of said antibody 2F2 comprise amino acid sequences of SEQ ID NO: 153, SEQ ID NO: 154, and SEQ ID NO: 155 respectively; wherein said $V_L$ CDR1, $V_L$ CDR2, $V_L$ CDR3 of said antibody 2F2 comprise amino acid sequences of SEQ ID NO: 162, SEQ ID NO: 163, and SEQ ID NO: 143 respectively.

In a specific embodiment, an antibody AB is provided ("AB" comprises $V_H$ CDRs of 2A6 and $V_L$ CDRs of 2B6, and also is referred to as "$V_H$2A6/$V_L$2B6"). Said $V_H$ CDR1, $V_H$ CDR2, and $V_H$ CDR3 of said antibody AB comprise amino acid sequences of SEQ ID NO: 120, SEQ ID NO: 121, and SEQ ID NO: 122 respectively; wherein said $V_L$ CDR1, $V_L$ CDR2, $V_L$ CDR3 of said antibody AB comprise amino acid sequences of SEQ ID NO: 135, SEQ ID NO: 136, and SEQ ID NO: 137 respectively. Alternatively, said $V_H$ CDR1, $V_H$ CDR2, and $V_H$ CDR3 of said antibody AB comprise amino acid sequences of SEQ ID NO: 144, SEQ ID NO: 145, and SEQ ID NO: 146 respectively; wherein said $V_L$ CDR1, $V_L$ CDR2, $V_L$ CDR3 of said antibody AB comprise amino acid sequences of SEQ ID NO: 158, SEQ ID NO: 159, and SEQ ID NO: 137 respectively.

In a specific embodiment, an antibody BA is provided ("BA" comprises $V_H$ CDRs of 2B6 and $V_L$ CDRs of 2A6, and also is referred to as "$V_H$2B6/$V_L$2A6"). Said $V_H$ CDR1, $V_H$ CDR2, and $V_H$ CDR3 of said antibody BA comprise amino acid sequences of SEQ ID NO: 123, SEQ ID NO: 124, and SEQ ID NO: 125 respectively; wherein said $V_L$ CDR1, $V_L$ CDR2, $V_L$ CDR3 of said antibody BA comprise amino acid sequences of SEQ ID NO: 132, SEQ ID NO: 133, and SEQ ID NO: 134 respectively. Alternatively, said $V_H$ CDR1, $V_H$ CDR2, and $V_H$ CDR3 of said antibody BA comprise amino acid sequences of SEQ ID NO: 147, SEQ ID NO: 148, and SEQ ID NO: 149 respectively; wherein said $V_L$ CDR1, $V_L$ CDR2, $V_L$ CDR3 of said antibody BA comprise amino acid sequences of SEQ ID NO: 156, SEQ ID NO: 157, and SEQ ID NO: 134 respectively.

In some embodiments, the present disclosure provides an isolated antibody or antigen binding fragment comprising $V_H$ CDRs and $V_L$ CDRs having any of the sequences as described elsewhere herein, and further comprising a $V_H$ region sequence having at least 90% identity to SEQ ID NO: 109, 110, 111, or 112; and a $V_L$ region sequence having at least 90% identity to SEQ ID NO: 113, 114, 115, or 116. In another embodiment, said identity is 95%, said identity is 98%, or said identity is 99%.

In some embodiments, the present disclosure provides an isolated antibody according to any of the embodiments disclosed herein, wherein the antibody further comprises a heavy chain and a light chain. In some embodiments, said heavy chain comprises a $V_H$ sequence having at least 90% identity to SEQ ID NO: 109, 110, 111, or 112; and said light chain comprises a $V_L$ region sequence having at least 90% identity to SEQ ID NO: 113, 114, 115, or 116. In another embodiment, said identity is 95%, said identity is 98%, or said identity is 99%.

In a specific embodiment, the present disclosure provides an antibody comprising the CDRs of antibody 2A6 and further comprising a $V_H$ region sequence having at least 90% identity to SEQ ID No: 109 and a $V_L$ region sequence having at least 90% identity to SEQ ID No: 113. In another embodiment, said identity is 95%, said identity is 98%, or said identity is 99%.

In a specific embodiment, the present disclosure provides an antibody comprising the CDRs of antibody 2B6 and further comprises a $V_H$ sequence having at least 90% identity to SEQ ID No: 110 and a $V_L$ sequence having at least 90% identity to SEQ ID No: 114. In another embodiment, said identity is 95%, said identity is 98%, or, said identity is 99%.

In a specific embodiment, the present disclosure provides an antibody comprising the CDRs of antibody 1E8 and further comprises a $V_H$ sequence having at least 90% identity to SEQ ID No: 111 and a $V_L$ sequence having at least 90% identity to SEQ ID No: 115. In another embodiment, said identity is 95%, said identity is 98%, or said identity is 99%.

In a specific embodiment, the present disclosure provides an antibody comprising the CDRs of antibody 2F2 and further comprises a $V_H$ sequence having at least 90% identity to SEQ ID No: 112 and a $V_L$ sequence having at least 90% identity to SEQ ID No: 116. In another embodiment, said identity is 95%, said identity is 98%, or said identity is 99%.

In a specific embodiment, the present disclosure provides an antibody comprising the CDRs of antibody AB and further comprises a $V_H$ sequence having at least 90% identity to SEQ ID No: 109 and a $V_L$ sequence having at least 90% identity to SEQ ID No: 114. In another embodiment, said identity is 95%, said identity is 98%, or said identity is 99%.

In a specific embodiment, the present disclosure provides an antibody comprising the CDRs of antibody BA and further comprises a $V_H$ sequence having at least 90% identity to SEQ ID No: 110 and a $V_L$ sequence having at least 90% identity to SEQ ID No: 113. In another embodiment, said identity is 95%, said identity is 98%, or said identity is 99%.

In another embodiment of any of the antibodies of the present disclosure, said antibody is modified so that it does not comprise an N-linked Glycosylation site in a variable region thereof. For instance, in some embodiments said antibody is modified by point mutation of the aspargine amino acid at position 76 (N76) of the $V_H$ region thereof. In one embodiment, N76 is mutated to alanine, arginine, aspartic acid, cysteine, glutamic acid, glutamine, glycine, histidine, isoleucine, leucine, lysine, methionine, phenylalanine, proline, serine, threonine, tryptophan, tyrosine, or valine. In a particular embodiment of the isolated antibodies disclosed herein, the antibody is modified by a point mutation of the aspargine amino acid at position 76 (N76) of the $V_H$ region thereof, wherein position N76 is mutated to alanine (A), or glutamine (Q).

In a particular embodiment of an antibody comprising no N-linked Glycosylation site in variable region, the present disclosure provides antibodies 2A6_A and 2A6_Q, wherein said N76 of the heavy chain is mutated to alanine and glutamine respectively. Accordingly, in one embodiment, the present disclosure provides an isolated antibody "2A6_Q" wherein $V_H$ comprises a sequence having at least 90% identity to SEQ ID NO: 164, wherein the amino acid at position 76 is A, or SEQ ID NO: 165, wherein the amino acid at position 76 is Q; and $V_L$ comprises a sequence having at least 90% identity to SEQ ID NO: 113. In another embodiment, said identity is 95%, said identity is 98%, or said identity is 99%.

In another embodiment, said isolated antibody specifically binds human IFN-γ with a binding value $K_D$ of less than $1\times10^{-8}$ M, less than $1\times10^{-9}$ M, less than $1\times10^{-10}$ M, less than $1\times10^{-11}$ M, or even less. Preferably, said binding value $K_D$ of IFN-γ is measured by bio-layer interferometry analysis.

In another embodiment, said isolated antibody inhibits human IFN-γ mediated activity with an $IC_{50}$ value of less than 50 ng/mL, less than 25 ng/mL, or less than 10 ng/mL. Preferably, said $IC_{50}$ value is measured by HLA-DR expression analysis.

In another embodiment, said antibody of the present disclosure might have cross-reactivity between species so that is convenient to be used for various purposes or for researches of different animal models. For example, in some embodiments said antibody may cross-react with IFN-γ from different mammalian species, such as from human, rhesus macaque/cynomolgus monkey.

In another embodiment, said isolated antibodies as described herein (e.g., 2A6, 2B6, 2A6_A, 2A6_Q, 1E8, 2F2, AB, BA, and antigen-binding fragments thereof) further comprise the characteristic of specifically binding to an epitope of human IFN-γ comprising one or more amino acid discontinuous amino acid sequences of the human IFN-γ of SEQ ID NO: 166. In one embodiment, the antibody can specifically bind an epitope comprising amino acids 30-52 and 78-92 of human IFN-γ. In one embodiment, the antibody can specifically bind an epitope comprising amino acids 36-48 and 82-92 of human IFN-γ.

The Second Aspect of the Present Disclosure.

In the second aspect of the present disclosure, another isolated antibody is provided. The antibody specifically binds to the same epitope as the antibody set forth in the first aspect of the present disclosure.

In a particular embodiment, the antibody specifically binds to one or more amino acid residues within amino acids 30-52 and 78-92 of human IFN-γ, wherein the amino acids 30-52 comprises amino acids of SEQ ID NO: 167, and the amino acids 78-92 comprises amino acids of SEQ ID NO: 168. In another embodiment, the antibody specifically binds to one or more amino acid residues within amino acids 36-48 and 82-92 of human IFN-γ, wherein said amino acids 36-48 comprises amino acids of SEQ ID NO: 171, and said amino acids 82-92 comprises amino acids of SEQ ID NO: 172.

In an alternative embodiment, said epitope comprises K43, Q48, and K86, of human IFN-γ; wherein said human IFN-γ comprises SEQ ID NO: 166. In another embodiment, said epitope comprises K37, E38, K43, Q46, Q48, K86, and R89 of human IFN-γ; wherein said human IFN-γ comprises SEQ ID NO: 166.

The Third Aspect of the Present Disclosure.

In the third aspect of the present disclosure, an isolated polynucleotide that encodes an antibody is provided. Specifically, said polynucleotide encodes said antibody of the first aspect and second aspect of the present disclosure. In a particular embodiment, said polynucleotide encodes said antibody 2A6, 2A6_A, 2A6_Q, 2B6, 1E8, 2F2, AB, or BA. For example, in some embodiments, the isolated polynucleotide encodes an antibody, wherein the antibody comprises a $V_H$ CDR1 comprising an amino acid sequence selected from SEQ ID NO: 120, 123, 126, 129, 144, 147, 150, or 153; $V_H$ CDR2 comprising an amino acid sequence selected from SEQ ID NO: 121, 124, 127, 130, 145, 148, 151, or 154; $V_H$ CDR3 comprising an amino acid sequence selected from SEQ ID NO: 122, 125, 128, 131, 146, 149, 152, or 155; $V_L$ CDR1 comprising an amino acid sequence selected from SEQ ID NO: 132, 135, 138, 141, 156, 158, 160, or 162; $V_L$ CDR2 comprising an amino acid sequence selected from SEQ ID NO: 133, 136, 139, 142, 157, 159, 161, or 163; and $V_L$ CDR3 comprising an amino acid sequence selected from SEQ ID NO: 134, 137, 140, or 143.

In a particular embodiment, said polynucleotide encoding said antibody 2A6 comprises sequences having at least 90% identity to SEQ ID NO: 173 and SEQ ID NO: 174. In a particular embodiment, said polynucleotide encoding said antibody 2A6_A comprises sequences having at least 90% identity to SEQ ID NO: 175 and SEQ ID NO: 174. In a particular embodiment, said polynucleotide encoding said antibody 2A6_Q comprises sequences having at least 90% identity to SEQ ID NO: 176 and SEQ ID NO: 174. In a particular embodiment, said polynucleotide encoding said antibody 2B6 comprises sequences having at least 90% identity to SEQ ID NO: 177 and SEQ ID NO: 178. In a particular embodiment, said polynucleotide encoding said antibody 1E8 comprises sequences having at least 90% identity to SEQ ID NO: 179 and SEQ ID NO: 180. In a particular embodiment, said polynucleotide encoding said antibody 2F2 comprises sequences having at least 90% identity to SEQ ID NO: 181 and SEQ ID NO: 182. In a particular embodiment, said polynucleotide encoding said antibody AB comprises sequences having at least 90% identity to SEQ ID NO: 173 and SEQ ID NO: 178. In a particular embodiment, said polynucleotide encoding said antibody BA comprises sequences having at least 90% identity to SEQ ID NO: 174 and SEQ ID NO: 177. In another embodiment, said identity is 95%, said identity is 98%, or said identity is 99%.

In another embodiment, said polynucleotide comprises a polynucleotide sequence comprising one or more codons selected for optimal expression of an antibody in a mammalian cell. This is another feature for improving the accuracy and efficiency of product. In a particular embodiment, said mammalian cell is a Chinese Hamster Ovary (CHO) cell, NSO cell, Baby hamster kidney (BHK) cell, SP2/0 cell, HEK 293 cell, HEK 293 EBNA cell, PER.C6® cell, and COS cell.

The Fourth Aspect of the Present Disclosure.

In the fourth aspect of the present disclosure, a vector and an isolated host cell comprising the same are provided. Said vector comprises a polynucleotide set forth in the third aspect of the present disclosure and is design to be carried by or expressed in any kind of host cells so that the antibody of the present disclosure can be produced. Said host cell is selected from the group consisting of E. coli, insect, yeast, or mammalian cells.

The Fifth Aspect of the Present Disclosure.

In the fifth aspect of the present disclosure, a composition comprising the antibody of the present disclosure is provided. In an embodiment, said composition is used for neutralizing IFN-γ's activity in vivo or in vitro. In another embodiment, said composition is a pharmaceutical composition for treating an IFN-γ mediated syndrome. Said "IFN-γ mediated syndrome" encompasses but not limited to, inflammation, Acquired Immune Deficiency Syndrome (AIDS), rheumatoid arthritis including juvenile rheumatoid arthritis, inflammatory bowel diseases including ulcerative colitis and Crohn's disease, multiple sclerosis, Addison's disease, diabetes (type I), epididymitis, glomerulonephritis, Graves' disease, Guillain-Barre syndrome, Hashimoto's disease, hemolytic anemia, systemic lupus erythematosus (SLE), lupus nephritis, myasthenia gravis, pemphigus, psoriasis, psoriatic arthritis, atherosclerosis, erythropoietin resistance, graft versus host disease, transplant rejection, autoimmune hepatitis-induced hepatic injury, biliary cirrhosis, alcohol-induced liver injury including alcoholic cirrhosis, rheumatic fever, sarcoidosis, scleroderma, Sjogren's syndrome, spondyloarthropathies, ankylosing spondylitis, kawasaki disease, dry eye disease, hemophagocytic lymphohistiocytosis, macrophage-activation syndrome, thyroiditis, vasculitis, or a combination thereof. The term "IFN-γ mediated syndrome" also encompasses any medical condition associated with increased levels of IFN-γ or increased sensitivity to IFN-γ.

In an embodiment, said composition comprises said antibody of the present disclosure and a carrier. Said antibody may be contained in an effective amount for the purpose of said composition. Said "effective amount" used herein is referred to the amount of each active agent required to confer the desired effect (ex. treating IFN-γ mediated syndrome of the present disclosure) on the subject, either alone or in combination with one or more other active agents. An effective amount varies, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Such antibody compositions can be prepared by mixing an anti-IFN-γ antibody of the present disclosure, having the desired degree of purity, with one or more carriers. Typically, such antibody compositions can be prepared as an aqueous solution (see e.g., U.S. Pat. No. 6,171,586, and WO2006/044908) or as a lyophilized formulation (see e.g., U.S. Pat. No. 6,267,958).

The carrier useful in the antibody compositions of the present disclosure can be a pharmaceutically acceptable carrier, which generally includes but is not limited to a buffer, excipient, stabilizer, preservatives, solvents, dispersion media, coatings, antibacterial and antifungal agents, isotonic and absorption delaying agents, and the like that are physiologically compatible. Preferably, the carriers should be suitable for intravenous, intramuscular, subcutaneous, parenteral, spinal or epidermal administration (e.g. by injection or infusion). Pharmaceutically acceptable carriers are generally nontoxic to subjects receiving them at the dosages and concentrations employed.

A wide range of such pharmaceutically acceptable carriers are well-known in the art (see e.g., Remington's Pharmaceutical Sciences 16th edition, Osol, A. Ed. (1980)). Exemplary pharmaceutically acceptable carriers useful in the antibody compositions of the present disclosure can include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn— protein complexes); and/or non-ionic surfactants such as polyethylene glycol (PEG).

Pharmaceutically acceptable carriers useful in the antibody compositions of the present disclosure can also include interstitial drug dispersion agents, such as soluble neutral-active hyaluronidase glycoproteins (sHASEGP) (see e.g., US Pat. Publ. Nos. 2005/0260186 and 2006/0104968), such as human soluble PH-20 hyaluronidase glycoproteins (e.g., rHuPH20 or HYLENEX®, Baxter International, Inc.).

Said composition can further include pharmaceutically acceptable excipient such as a disintegrating agent, a binder, a lubricant, a preservative, or a combination thereof.

The Sixth Aspect of the Present Disclosure.

In the sixth aspect of the present disclosure, a method for treating an IFN-γ mediated syndrome is provided. Said method comprises administering to a subject in need thereof an effective amount of an antibody of the present disclosure. Said subject in need could be a patient (i.e., human) who suffers an IFN-γ mediated syndrome. Said IFN-γ mediated syndrome can be construed as described above but is not limited to the conditions or diseases listed above. Accordingly, in some embodiments, the antibodies of the present disclosure are formulated for administration as a pharmaceutical composition, wherein said composition comprises an antibody as disclosed herein and pharmaceutically acceptable carrier. Any of the pharmaceutically acceptable carriers known in the art for use with antibodies can be used in this aspect of the disclosure including, but not limited to, water, PBS, salt solutions, gelatins, oils, alcohols, or a combination thereof.

It is contemplated that any of the methods known in the art for administering pharmaceutical compositions comprising antibodies can be used to administer the pharmaceutical compositions of the present disclosure. Accordingly, in some embodiments of this sixth aspect of the disclosure, said administering is by any mode that delivers the antibody to the subject systemically, or to a desired target tissue. Systemic administration generally refers to any mode of administration of the antibody into a subject at a site other than directly into the desired target site, tissue, or organ, such that the antibody or formulation thereof enters the subject's circulatory system and, thus, is subject to metabolism and other like processes.

Accordingly, modes of administration useful in the methods of treatment of the present disclosure can include, but are not limited to, injection, infusion, instillation, and inhalation. Administration by injection can include intravenous, intramuscular, intraarterial, intrathecal, intraventricular, intracapsular, intraorbital, intracardiac, intradermal, intraperitoneal, intravitreal, transtracheal, subcutaneous, subcuticular, intraarticular, subcapsular, subarachnoid, intraspinal, intracerebro spinal, and intrasternal injection and infusion.

Said antibody can be administered with a pharmaceutically acceptable carrier. Said pharmaceutically acceptable carrier includes but not limited to water, PBS, salt solutions, gelatins, oils, alcohols, or a combination thereof.

The Seventh Aspect of the Present Disclosure.

In the seventh aspect of the present disclosure, a method for detecting IFN-γ in an environment is provided. Said method could be used in a laboratory for detecting the existence of IFN-γ in a sample. In another embodiment, said method could be used for quantification of IFN-γ in a sample. Said method comprises (A) applying an antibody of the present disclosure; (B) incubating said environment with an anti-IgG antibody; wherein said anti-IgG antibody is conjugated with a detectable label; and (C) detecting said detectable label. In a specific embodiment, said method is parts of Western Blot or enzyme-linked immunosorbent assay (ELISA). In a specific embodiment, said anti-IgG antibody is a Fc-specific antibody.

In a specific embodiment, said environment is a container, a membrane, or a plate comprising a sample. Said detectable label is referred to a molecule conjugated with said anti-IgG antibody for detection purpose. Said detectable label includes but not limited to a peroxidase, alkaline phosphatase, beta-Galactosidase, fluorescent tags or a combination thereof. In a specific embodiment, said detectable label is a peroxidase; and said method further comprises incubating said environment with a p-Nitrophenyl phosphate solution (in another embodiment, TMB solution is used) after step (B) and before step (C). In this specific embodiment, through a color reaction, IFN-γ can be detected and quantification by observation at $OD_{405}$.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1. Preparation of the Recombinant Anti-IFN-γ Antibodies

Isolation of Single Human B Cells by Fluorescence Activated Cell Sorting.

Peripheral venous blood samples were collected from human patients with mycobacterial diseases after signed informed consent in accordance with Institutional Review Board (IRB)-reviewed protocols. Mononuclear cells were isolated from the peripheral venous blood of the patients after being purified by Ficoll-Paque (GE Healthcare) density gradient centrifugation according to the manufacturer's instructions. The purified mononuclear cells were resuspended in 5% normal mouse serum (Jackson ImmunoResearch) of FACS buffer (1% FBS, 2 mM EDTA, 0.1% NaN₃ in PBS) with the concentration of 1×10⁷ cells/mL and placed on ice for 30 minutes. Meanwhile, 20 µg/mL anti-human CD119 antibody (BioLegend) was added to the cells. Then, aliquots of 1×10⁶ cells were washed with FACS buffer and added with 1 µg recombinant IFN-γ protein (R&D systems) within 1×10⁶ cells for 20 minutes on ice. Before the sorting process, cells were stained on ice with anti-human IgG PE (BD bioscience), anti-human IgD APC (BD bioscience), anti-human CD3 PE-Cyanine7 (eBiosciense), anti-human CD19 APC-eFluor 780 (eBioscience), anti-human IFN-γ FITC (BD Bioscience), and 7-Aminoactinomycin D (Sigma) as a DNA marker for 30 minutes. Individual single B cells binding to IFN-γ were gated on CD19⁺IgG⁺CD3⁻IgD⁻FITC⁺ and then sorted into individual wells of 96-well plates containing 18 µL/well of a RT-lysis buffer (which contains 200 ng random hexamer primer (Thermo Scientific), 1 µL of dNTP-mix (Thermo Scientific), 0.5% v/v Igepal CA-630 (Sigma), and 40U Ribolock (Fermentas)), thereby obtaining a lysate mixture having the total RNA of single B cells. The 96-well plates were sealed with aluminum sealing tape (Corning) and immediately stored at −80° C.

Single Cell RT-PCR and Immunoglobulin (Ig) Gene Amplification.

cDNA was synthesized in a total volume of 20 µL/well in the above 96-well plate which included 2 µL (50 U) Maxima H minus reverse transcriptase (Thermo Scientific) in DEPC-treated water into each well. The total RNA of each B cell that bound to IFN-γ was subjected to reverse transcription (RT) reaction, which was performed at 42° C. for 10 minutes in an annealing step, at 25° C. for 10 minutes in a pre-primer extension step, at 50° C. for 45 minutes in a polymerization step, and at 85° C. for 5 minutes in an enzyme inactivation step. The first strand cDNA thus formed was stored at −20° C.

IgH, Igλ, Igκ V gene transcripts of each B cell were amplified by nested-PCR, with each nested-PCR involving a first round PCR starting from 2.5 µL of the first strand cDNA obtained above as a template, and then a second round PCR using 2.5 µL of unpurified first round PCR product obtained from the first round PCR as a template. All PCR reactions were performed in a total volume of 25 µL per reaction containing 0.5 µM primer mix, with details of the primer mix listed in Table 1 (See primer listing), 200 µM each dNTP (Thermo Scientific) and 0.5 U Phusion High-Fidelity DNA polymerase (Thermo Scientific). All PCR reactions were performed with DEPC-treated water. Each of the first and second rounds of the nested PCR reaction was performed for 35 cycles at 98° C. for 10 seconds in a denaturation step, at 65° C. for 15 seconds in an annealing step, and at 72° C. for 30 seconds in an elongation step.

TABLE 1

| Nested-PCR | Primers | IgH V gene | Igκ V gene | Igλ V gene |
| --- | --- | --- | --- | --- |
| First round | forward primers (SEQ ID NOs:) | 1-13 | 24-31 | 40-51 |
|  | reverse primers (SEQ ID NOs:) | 63 | 65 | 67 |
| Second round | forward primers (SEQ ID NOs:) | 14-23 | 32-39 | 52-62 |
|  | reverse primers (SEQ ID NOs:) | 64 | 66 | 68 |

Ig V Gene Sequence Analysis.

Aliquots of the $V_H$, $V_κ$ and $V_λ$ chain PCR product of each B cell (obtained from the second round PCR as mentioned above) were purified with QIAquick PCR purification kit (Qiagen) according to the manufacturer's instructions and sequenced with the primers identified by SEQ ID NO: 64, SEQ ID NO: 66 and SEQ ID NO: 69, respectively (see primer listing). The obtained sequences were analyzed by IMGT®, the international ImMunoGeneTics information System® (http://www.imgv.org), to identify germline V(D)J gene segments with highest identity.

The amino acid sequences of the heavy chain variable region ($V_H$) and the light chain variable region ($V_L$) encoded by the obtained Ig V gene sequences were shown and aligned with each other in primer listing, in which the framework regions and complementarity-determining regions (CDRs) thereof, as determined by IMGT or Kabat system.

Expression Vector Cloning.

After sequencing, the gene-specific primers (see primer listing) were chosen according to the V or J segments with highest identity (see Table 2) to conduct a further PCR reaction under the similar reaction condition as that of the nested PCR, in which the $V_H$, $V_\kappa$ and $V_\lambda$ chain PCR products of each B cell (obtained from the second round PCR as mentioned above) were used as templates. The obtained PCR products were purified as described above and cloned into human $IgG_1\lambda$ expression vectors (kindly provided from Dr. Tse-Wen Chang in Academia Sinica, Taiwan), so as to obtain four expression vectors for the four antibodies identified as "2A6" "2B6," "2F2," and "1E8."

TABLE 2

| Antibody | $V_H$ chain Forward primer/reverse primer (SEQ ID NO:) | $V_L$ chain |
|---|---|---|
| 2A6 | 70/80 | 102/106 |
| 2B6 | 70/80 | 102/106 |
| 2F2 | 70/83 | 96/106 |
| 1E8 | 75/80 | 100/106 |

Besides the above four expression vectors, the vectors for expression of the combination of 2A6 $V_H$ heavy chain and 2B6 $V_L$ light chain (designated VH2A6/$V_L$2B6, named as "AB") and the combination of 2B6 $V_H$ heavy chain and 2A6 $V_L$ light chain (designated VH2B6/VL2A6, named as "BA") were also constructed.

The DNA of $V_H$ and $V_L$ of AMG811 were synthesized using GeneArt Gene Synthesis (Thermo Fisher). The vector for expression of AMG811 was constructed using PCR based cloning described above.

Recombination was carried out by GeneArt® Seamless Cloning and Assembly Enzyme Mix (Invitrogen). Competent E. coli were transformed at 42° C. with 5 μL of recombination product. Colonies of the transformed E. coli were screened by PCR using $pIgG_1\kappa$-screen+ (SEQ ID NO:

117) or $pIgG_1\lambda$-screen+(SEQ ID NO: 118) as the forward primer and pIgG1-screen− (SEQ ID NO: 119) as the reverse primer, respectively (see primer listing). PCR products of the expected size (about 1,800 bps) were sequenced for confirmation of identity with the original PCR products. Plasmid DNA was isolated using QIAprep® Spin columns (Qiagen) from 3 mL bacterial cultures of the transformed E. coli grown for 16 hours at 37° C. in Luria-Bertani broth containing 100 μg/mL ampicillin Recombinant Antibody Production.

FreeStyle™ 293-F cells (Thermo Scientific, R79007) were cultured in a 250-mL flask containing FreeStyle™ 293 expression medium (Gibco, 12338018) under standard conditions with the concentration of $1 \times 10^6$ cells. Transient transfection of the exponentially growing FreeStyle™ 293-F cells ($1.5 \sim 2 \times 10^6$ cells/ml) were performed by linear polyethylenimine (PEI) with an average molecular weight of 25 kDa (Polysciences, Warrington, Pa.) as a transfection reagent and a total of 88 μg of the plasmid DNA. After transfection, the cells were cultured for 3 days and the culture medium was harvested. The culture medium was centrifuged for 10 min at 3000 rpm to remove the FreeStyle™ 293-F cell debris and afterward, the resultant supernatant was collected and filtered through a 0.45 μm filter.

Recombinant Antibody Purification.

The resultant supernatants as obtained above were subsequently purified with Protein A Sepharose Fast Flow beads (GE Healthcare, 17-1279-01) so as to obtain the recombinant antibodies. In brief, 80 mL of the supernatants were added with 80 μL Protein A Sepharose Fast Flow beads and aliquoted evenly into two 50-ml tubes which were incubated for 24 hours at 4° C. under rotation. Then, the tubes were centrifuged at 3000 rpm for 10 min, and afterward, the resultant supernatants were removed and the beads were equilibrated with PBS. The equilibrated beads were eluted with 0.1 M glycine (pH 3.0), and the eluates were collected in tubes containing 1 M Tris (pH 8.0) and dialyzed against PBS buffer, so as to obtain the recombinant antibodies.

For clarity, the CDRs on the $V_H$ chain and $V_L$ chain of each of the monoclonal antibodies are summarized in Table 3 and Table 4, respectively. CDRs were identified based on both the Kabat and the IMGT systems by sequence annotation and by internet-based sequence analysis (http://www.imgt.org/IMGT_vquest/share/textes/index.html and http://www.ncbi.nlm.nih.gov/igblast/). In Tables 3 and 4 below, CDRs following "K:" indicate Kabat system used, and CDRs following "I:" indicate IMGT system used.

TABLE 3

| Antibody | $V_H$ CDR1 | $V_H$ CDR2 | $V_H$ CDR3 |
|---|---|---|---|
| 2A6 | I: GFTFSNYF (SEQ ID No. 120) K: GFTFSNYFIH (SEQ ID No. 144) | I: ISGRTKYM (SEQ ID No. 121) K: TISGRTKYMFYSDSLRG (SEQ ID No. 145) | I: VRGYDHSDSNSAADLLH (SEQ ID No. 122) K: GYDHSDSNSAADLLH (SEQ ID No. 146) |
| 2B6 | I: GFPFSRYS (SEQ ID No. 123) K: GFPFSRYSMH (SEQ ID No. 147) | I: MTSRTNHK (SEQ ID No. 124) K: SMTSRTNHKYYADSLKG (SEQ ID No. 148) | I: ARGYDTSGSDSGVDFQY (SEQ ID No. 125) K: GYDTSGSDSGVDFQY (SEQ ID No. 149) |
| 1E8 | I: GFTFSIYS (SEQ ID No. 126) K: GFTFSIYSMN (SEQ ID No. 150) | I: ISGSGDNT (SEQ ID No. 127) K: SISGSGDNTYYADSVKG (SEQ ID No. 151) | I: AKSGRNIISPGFDS (SEQ ID No. 128) K: SGRNISPGFDS (SEQ ID No. 152) |

TABLE 3-continued

| Antibody | V_H CDR1 | V_H CDR2 | V_H CDR3 |
|---|---|---|---|
| 2F2 | I: GFNFSDYY (SEQ ID No. 129) K: GFNFSDYYMT (SEQ ID No. 153) | I: ISNSGSHT (SEQ ID No. 130) K: YISNSGSHTYYADAVKG (SEQ ID No. 154) | I: ARDPSIMRGTYYMDV (SEQ ID No. 131) K: DPSIMRGTYYMDV (SEQ ID No. 155) |
| VH2A6/ VL2B6 | I: GFTFSNYF (SEQ ID No. 120) K: GFTFSNYFIH (SEQ ID No. 144) | I: ISGRTKYM (SEQ ID No.121) K: TISGRTKYMFYSDSLRG (SEQ ID No. 145) | I: VRGYDHSDSNSAADLLH (SEQ ID No.122) K: GYDHSDSNSAADLLH (SEQ ID No. 146) |
| VH2B6/ VL2A6 | GFPFSRYS (SEQ ID No. 123) K: GFPFSRYSMH (SEQ ID No. 147) | MTSRTNHK (SEQ ID No. 124) K: SMTSRTNHKYYADSLKG (SEQ ID No. 148) | ARGYDTSGSDSGVDFQY (SEQ ID No. 125) K: GYDTSGSDSGVDFQY (SEQ ID No. 149) |

TABLE 4

| Antibody | V_L CDR1 | V_L CDR2 | V_L CDR3 |
|---|---|---|---|
| 2A6 | I: SGSVASHY (SEQ ID No. 132) K: VRSSGSVASHYVQ (SEQ ID No. 156) | I: EDS (SEQ ID No. 133) K: EDSHRPS (SEQ ID No. 157) | I: QSYYGNNQVL (SEQ ID No. 134) K: QSYYGNNQVL (SEQ ID No. 134) |
| 2B6 | I: RGYIASYY (SEQ ID No. 135) K: TRGRGYIASYYVQ (SEQ ID No. 158) | I: EDT (SEQ ID No. 136) K: EDTQRPS (SEQ ID No. 159) | I: QSYDDANHVI (SEQ ID No. 137) K: QSYDDANHVI (SEQ ID No. 137) |
| 1E8 | I: SDYGDYK (SEQ ID No. 138) K: TLNSDYGDYKVD (SEQ ID No. 160) | I: VGTGGIVG (SEQ ID No. 139) K: VGTGGIV (SEQ ID No. 161) | I: GADHGSANNFIWV (SEQ ID No. 140) K: GADHGSANNFIWV (SEQ ID No. 140) |
| 2F2 | I: SSNIGTNP (SEQ ID No. 141) K: SGSSSNIGTNPVS (SEQ ID No. 162) | I: FNN (SEQ ID No. 142) K: FNNQRPS (SEQ ID No. 163) | I: ASWDDTLNGLV (SEQ ID No. 143) K: ASWDDTLNGLV (SEQ ID No. 143) |
| VH2A6/ VL2B6 | I: RGYIASYY (SEQ ID No. 135) K: TRGRGYIASYYVQ (SEQ ID No. 158) | I: EDT (SEQ ID No. 136) K: EDTQRPS (SEQ ID No. 159) | I: QSYDDANHVI (SEQ ID No. 137) K: QSYDDANHVI (SEQ ID No. 137) |
| VH2B6/ VL2A6 | I: SGSVASHY (SEQ ID No. 132) K: VRSSGSVASHYVQ (SEQ ID No. 156) | I: EDS (SEQ ID No. 133) K: EDSHRPS (SEQ ID No. 157) | I: QSYYGNNQVL (SEQ ID No. 134) K: QSYYGNNQVL (SEQ ID No. 134) |

Cloning and Analysis of Single Site Glycosylation Mutants.

When antibody 2A6 was expressed in mammalian cells, two bands of heavy chains were observed (FIG. 1, lane 1). This is possible due to posttranslational modification. The consensus sequence for N-linked glycosylation is Asn-Xaa-Ser/Thr and more rarely Asn-X-Cys. Monoclonal antibodies have one conserved N-linked glycosylation at the Fc part at position N297. It was noted that the antibody 2A6 comprises one N-linked glycosylation site at its variable region (76th amino acid of the heavy chain thereof).

The presence of N-linked glycosylation site was confirmed by PNGase F digestion assay. Briefly, 3.5 μg of antibody, 1 μl of Glycoprotein Denaturing Buffer (10×) and H_2O (if necessary) were mixed to make a 15 μl total reaction volume. The antibody was heated at 100° C. for 10 minutes for denature purpose. The denatured antibody was then chilled on ice and centrifuged for 10 seconds. A total reaction mixture (30 μl) was prepared by adding 3 μl of GlycoBuffer 2 (10×), 3 μl of 10% NP-40 and 9 μl of H_2O. The reaction mixture was incubated at 37° C. for 1 hour and then analyzed by SDS-PAGE. Deglycosylation of antibodies was determined by the mobility shifts.

Following PNGase F digestion, antibody 2A6 had reduced size indicating that N-linked carbohydrate was removed. Only a single clear band of heavy chain with a lower apparent molecular mass was detected (FIG. 1, lane 2). This suggest that the lower band of heavy chain observed before PNGase F treatment is due to partial glycosylation of an N-linked Glycosylation site.

This N-linked glycosylation site is considered as a partial glycosylation site and would make the mass production of antibody 2A6 lack of molecular homogeneity. In order to facilitate the commercial utility of antibody 2A6, point mutation was designed and conducted to remove the aforesaid N-linked glycosylation site.

To generate site-specific glycosylation mutant plasmids, site-directed mutagenesis was performed using Q5 polymerase from NEB. The oligonucleotides used for mutagenesis of each construct are as follows (sense sequence): c2A6_Q 5'-CGTTTCTAGAGACAACGCCCAGAAT-TCGGTATATCTCCACA-3' (SEQ ID NO: 169) and c2A6_A 5'-CGTTTCTAGAGACAACGCCGCCAAT-TCGGTATATCTCCAC-3' (SEQ ID NO: 170). Mutant sequences were then verified by DNA sequencing of each construct. After the aforesaid point mutation, The 76th amino acid of the heavy chain variable region of antibody 2A6 was mutated from Asparagine to Glutamine or Alanine naming antibody 2A6_Q (carries a N76Q mutation on its heavy chain) and antibody 2A6_A (carries N76A mutation on its heavy chain). Consequently, the heavy chains of antibody 2A6_Q and antibody 2A6_A comprises SEQ ID NO: 165 and SEQ ID NO: 164 respectively.

Figure 2:
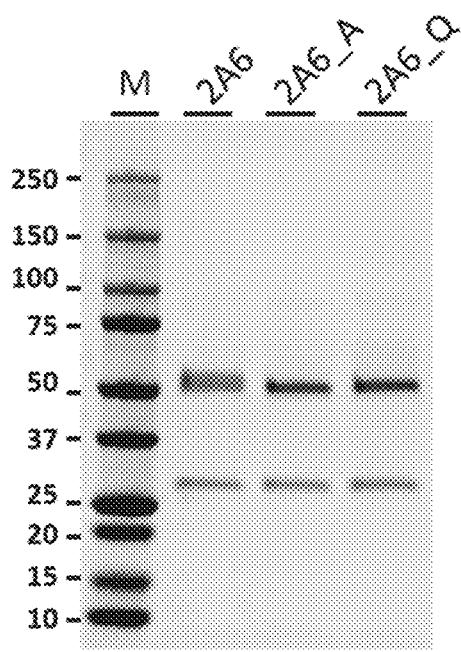
FIG. 2 shows the result of the SDS-PAGE analysis of antibody 2A6, 2A6_A and 2A6_Q in Example 1.

Turning to antibody 2A6_A and antibody 2A6_Q, SDS-PAGE analysis showed that the heavy chain of 2A6 showed two bands, whereas the heavy chain of 2A6_A or 2A6_Q showed a sharp single band with a lower molecular mass (FIG. 2). These data suggest that N-linked glycosylation site was disrupted in 2A6_Q and 2A6_A. The glycosylation status of 2A6, 2A_Q and 2A6_A was further studied using Mass spectrometry analysis. A UPLC system consisted of an Acquity H-class bio system with a quaternary UPLC pump (QSM), automatic sample injection device (SM) equipped with 50 ul sample loop and a photodiode array detector (Waters). Chromatograms were processed using Masslynex software (V4.1, Waters). N-linked glycosylation Asn-76 of 2A6 was confirmed. Replace of Asn-76 with Ala (2A6_A) or Gln (2A6_Q) resulted in loss of this glycosylation signal.

Example 2. Determination of the Activity of the Recombinant Anti-IFN-γ Antibodies Experimental Procedure:
A. Bio-Layer Interferometry (BLI) Analysis.

Antibody-binding kinetic rate constants ($k_a$ and $k_d$) were measured by Bio-Layer Interferometry (BLI, ForteBio Octet RED96). The BLI assay was performed using AHC (Anti-hIgG Fc Capture) biosensors (ForteBio) to capture each anti-IFN-γ mAbs (750 ng/mL) to acquire a 0.5 nm shift and then the biosensors were dipped into varying concentrations (i.e. 0, 0.625, 1.25, 2.5, 5, 10, 20 and 40 nM) of recombinant human IFN-γ protein (R&D systems, 285-IF-100) in running buffer containing 0.1% bovine serum albumin (BSA), 0.1% Tween-20, 250 mM NaCl, 2.7 mM KCl, 10 mM $Na_2HPO_4$ and 1.8 mM $KH_2PO_4$ in sterile water. Rate constants were calculated by curve fitting analyses (1:1 Langmuir model) of binding response with a 5-minute association and 15-minute dissociation interaction time.
B. HLA-DR Expression.

$2 \times 10^5$ THP-1 cells (BCRC 60430) were cultured in 100 μL of Roswell Park Memorial Institute (RPMI)-1640 medium (Gibco, 11875-093) supplemented with 10% FBS and 1% penicillin/streptomycin, and then treated with different concentrations (i.e. 0.017, 0.05, 0.15, 0.45, 1.37, 4.11, 12.34, 37.03, 111.1, 333.3, 1000, 3000, 5000 and 10000 ng/mL) of 2A6, 2B6, 1E8 and 2F2 anti-IFN-γ mAbs for 30 min. The treated THP-1 cells were stimulated with 2 ng/mL recombinant human IFN-γ protein and cultivated in an incubator (37° C., 5% $CO_2$) for 24 hours. The un-stimulated THP-1 cells were used as control. Thereafter, the stimulated and un-stimulated THP-1 cells were stained with HLA-DR-PE antibody (BD Pharmigen™) and then placed for 30 minutes on ice in the dark. The stained cells were washed with 2 mL of PBS and resuspended in 500 μL of PBS. The fluorescence intensity of the stained cells was acquired with a FACSVerse flow cytometer and analyzed with FACSuite software. The inhibition percentage of HLA-DR expression for each antibody is obtained by the following formula:

$A = (B/C) \times 100$ where A=Inhibition percentage of HLA-DR expression; B=the median value of the fluorescence intensity for the stimulated cells; C=the median value of the fluorescence-intensity for the unstimulated cells
C. ELISA Assay of Anti-IFN-γ Antibody.

A clear polystyrene 96-well, flat-bottomed plate (Nunc) was coated with 100 μL of recombinant human IFN-γ protein (2 μg/mL) or BSA (2 μg/mL) in bicarbonate buffer (pH 9.6) per well and incubated at 4° C. overnight. The plate was washed three times using phosphate-buffered saline (PBS) with 0.05% Tween 20 and then blocked with 5% human normal serum albumin (Aventis) in PBS for 2 hours at 25° C. The plate was washed again using PBS with 0.05% Tween 20, after which each of 1E8, 2F2, 2A6, 2B6, AB and BA mAbs in two different concentrations of 1 μg/mL and 0.1 μg/mL were added into the wells of the plate for binding with the recombinant human IFN-γ protein, followed by reaction at 25° C. for 2 hours. The plate was thoroughly washed using PBS with 0.05% Tween 20, and then Fc-specific alkaline phosphatase-conjugated AffiniPure Goat anti-human IgG (Cappel) was added at a dilution ratio of 1:2500. The plate was placed for 90 minutes at 37° C. and then washed five times using PBS with 0.05% Tween 20. After adding p-Nitrophenyl phosphate (pNPP) solution (100 μL/well), the plate was placed at 37° C. for 30 minutes. Absorbance was determined at $OD_{405}$ nm with a VICTOR X3 Multilabel Plate Reader (PerkinElmer).
Results:
A. Bio-Layer Interferometry Analysis.

Figure 3:
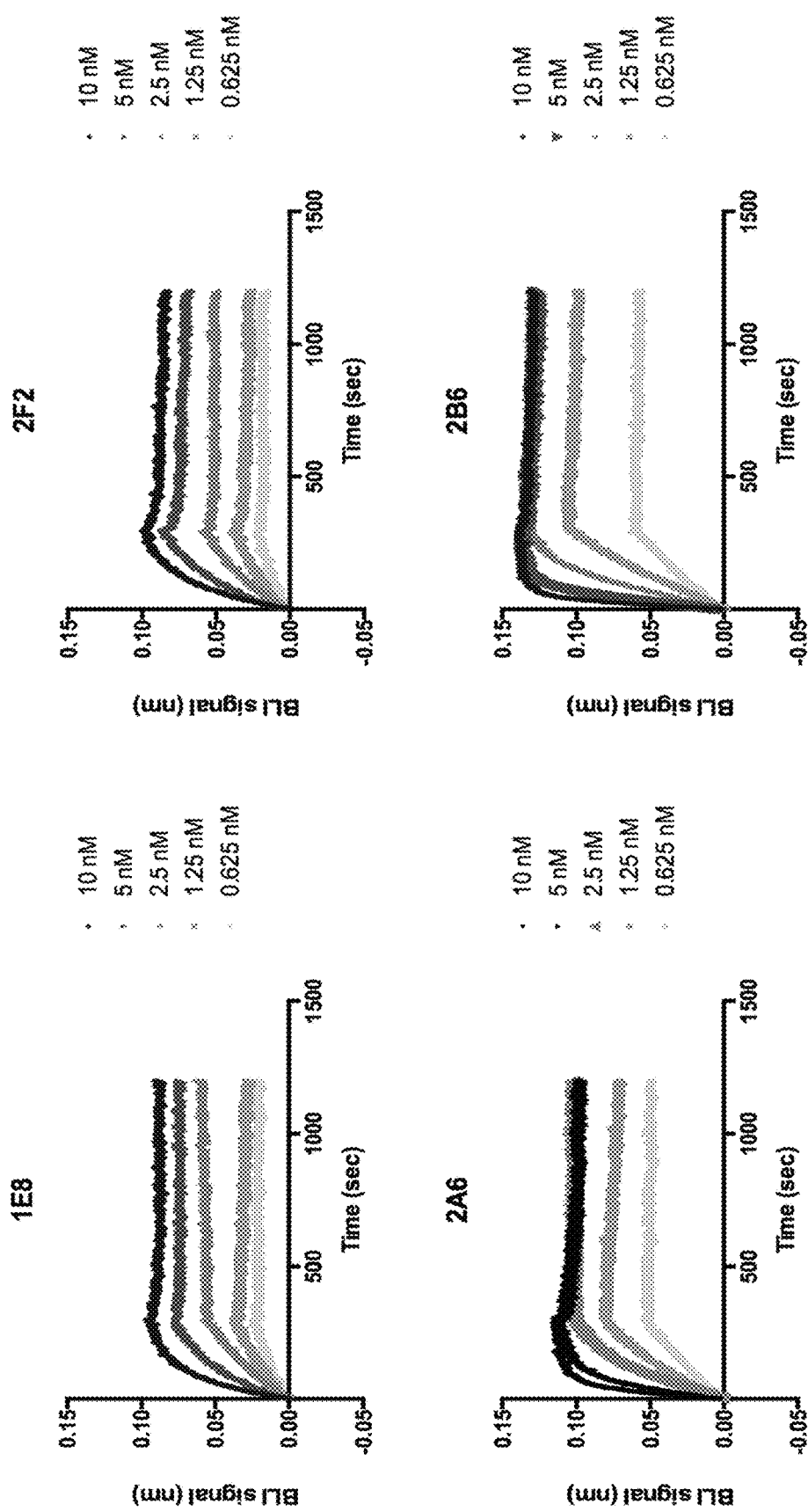
FIG. 3 shows the binding curves obtained by passing different concentrations of recombinant human IFN-γ (0, 0.625, 1.25, 2.5, 5, 10 nM) over anti-IFN-γ mAbs immobilized on the AHC biosensors in Example 2.

FIG. 3 shows the binding curves obtained by passing different concentrations of recombinant human IFN-γ (0, 0.625, 1.25, 2.5, 5, 10 nM) over anti-IFN-γ mAbs immobilized on the AHC biosensors. Antibody-binding kinetic rate constants ($K_a$ and $K_d$), as well as the equilibrium dissociation constant ($K_D = K_d/K_a$), are displayed in Table 5.

Referring to Table 5, it can be seen that the recombinant 2A6, 2B6, 1E8 and 2F2 antibodies have a low $K_D$ value, indicating that the recombinant antibodies of the present disclosure have high affinity to human IFN-γ.

TABLE 5

| mAb | $K_a$ (1/Ms) | $K_d$ (1/s) | $K_D$ (M) |
|---|---|---|---|
| 2A6 | $1.08 \times 10^6$ | $3.97 \times 10^{-5}$ | $3.68 \times 10^{-11}$ |
| 2B6 | $1.48 \times 10^6$ | $1.08 \times 10^{-4}$ | $7.31 \times 10^{-11}$ |
| 1E8 | $4.64 \times 10^5$ | $1.21 \times 10^{-4}$ | $2.61 \times 10^{-10}$ |
| 2F2 | $3.44 \times 10^5$ | $1.09 \times 10^{-4}$ | $3.17 \times 10^{-10}$ |

Figure 4:
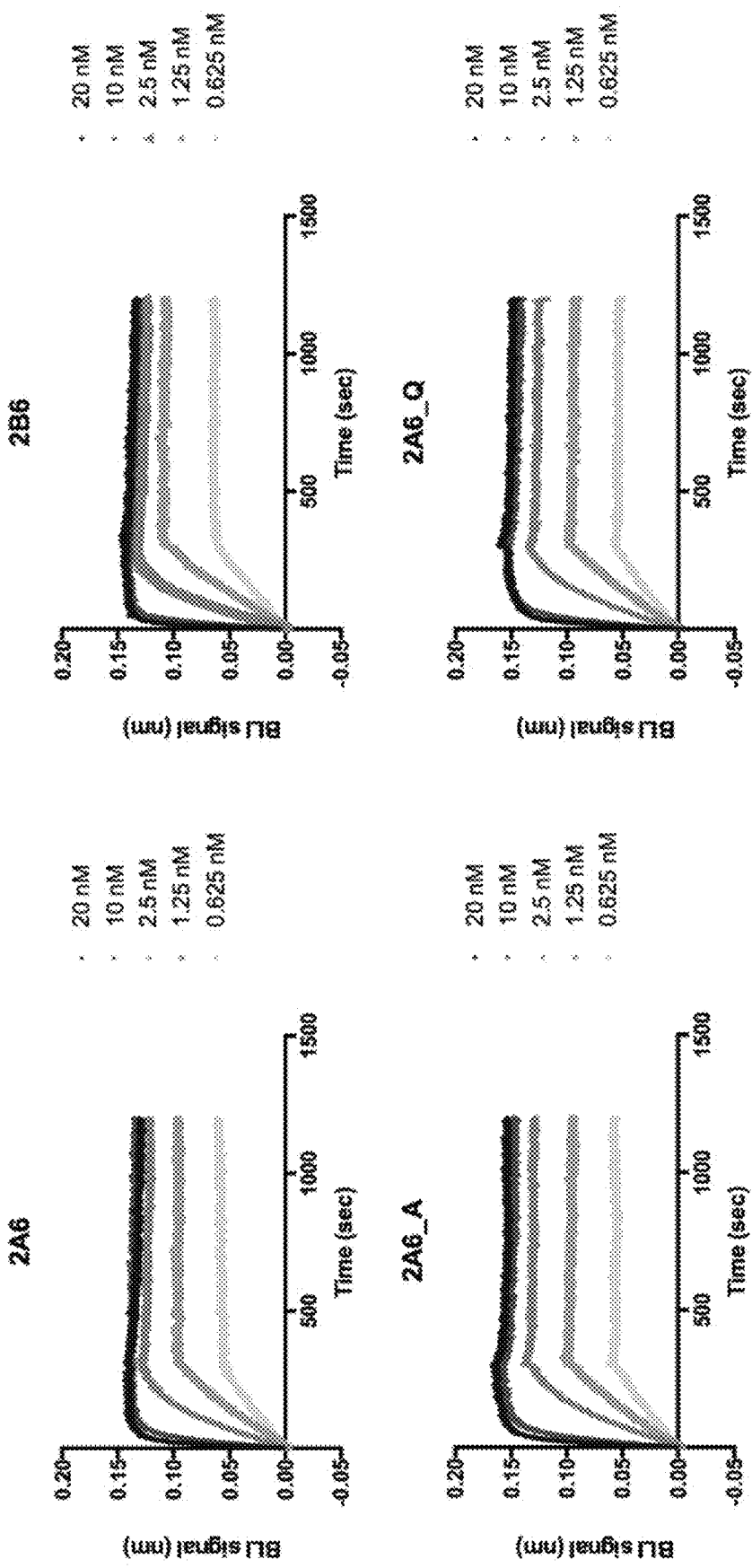
FIG. 4 shows the binding curves obtained by passing different concentrations of recombinant human IFN-γ (0, 0.625, 1.25, 2.5, 5, 10, 20 nM) over anti-IFN-γ mAbs immobilized on the AHC biosensors in Example 2. AMG811 is an anti-IFN-γ antibody described in U.S. Pat. No. 7,335,743 and was prepared as described therein. Control Ab is human IgG1 isotype control antibody (Bio X cell; BP0297).
Figure 4:
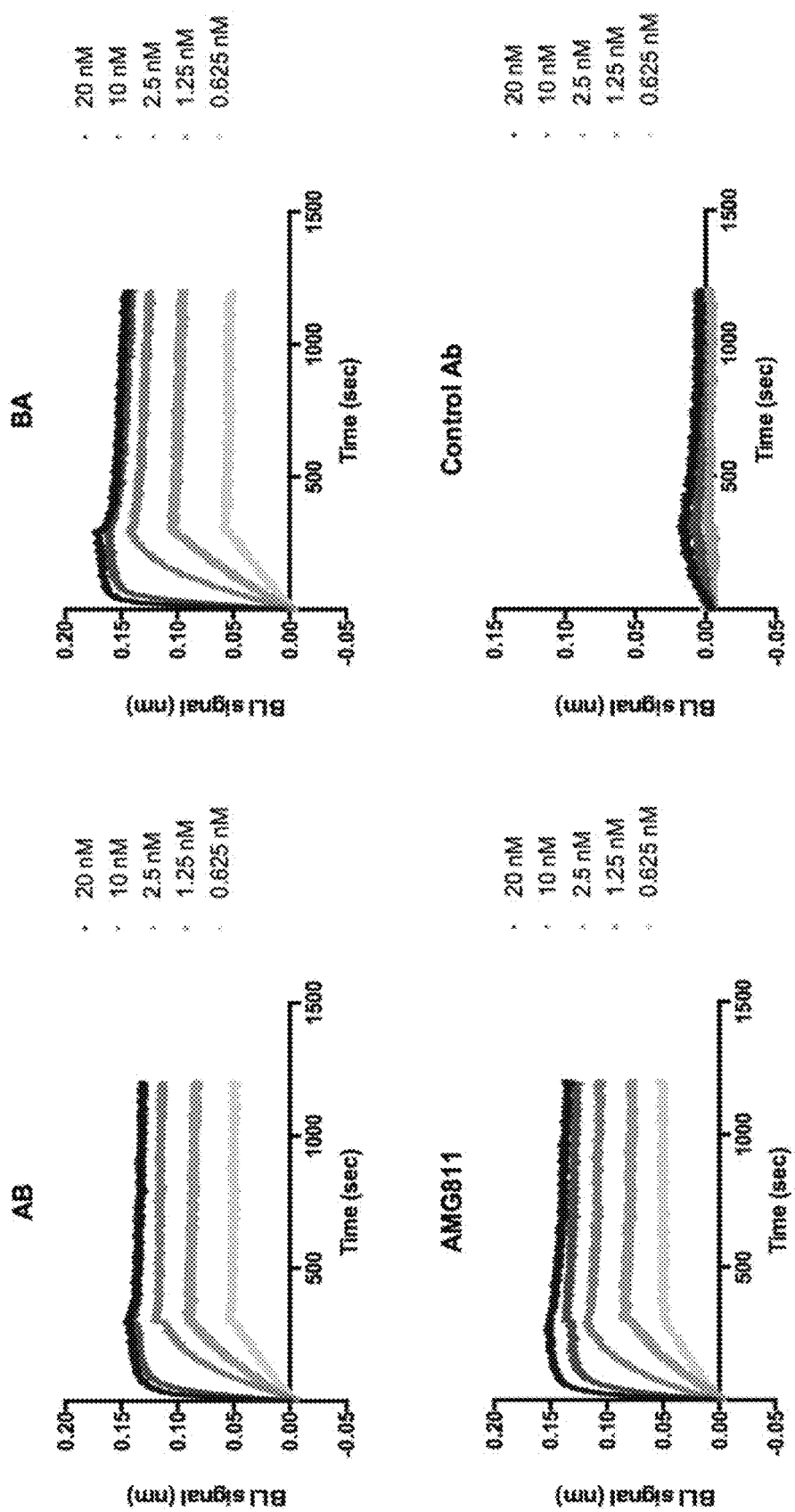

Another experiment including AMG811 (AMG811 is an anti-IFN-γ antibody described in U.S. Pat. No. 7,335,743 and was prepared as described therein), 2A6, 2B6, 2A6_A, 2A6_Q, AB, and BA antibodies showed that the antibodies of the present disclosure exhibited comparable or even better anti-IFN-γ activity than AMG811 (FIG. 4 and Table 6).

TABLE 6

| mAb | $K_a$ (1/Ms) | $K_d$ (1/s) | $K_D$ (M) |
|---|---|---|---|
| AMG811 | $2.48 \times 10^6$ | $8.59 \times 10^{-5}$ | $3.47 \times 10^{-11}$ |
| 2A6 | $2.61 \times 10^6$ | $4.90 \times 10^{-5}$ | $1.87 \times 10^{-11}$ |
| 2B6 | $3.13 \times 10^6$ | $5.40 \times 10^{-5}$ | $1.72 \times 10^{-11}$ |
| 2A6_A | $2.32 \times 10^6$ | $5.17 \times 10^{-5}$ | $2.23 \times 10^{-11}$ |
| 2A6_Q | $2.41 \times 10^6$ | $5.23 \times 10^{-5}$ | $2.17 \times 10^{-11}$ |
| AB | $2.19 \times 10^6$ | $5.46 \times 10^{-5}$ | $2.50 \times 10^{-11}$ |
| BA | $2.76 \times 10^6$ | $1.31 \times 10^{-4}$ | $4.75 \times 10^{-11}$ |

B. HLA-DR Expression.

Figure 5:
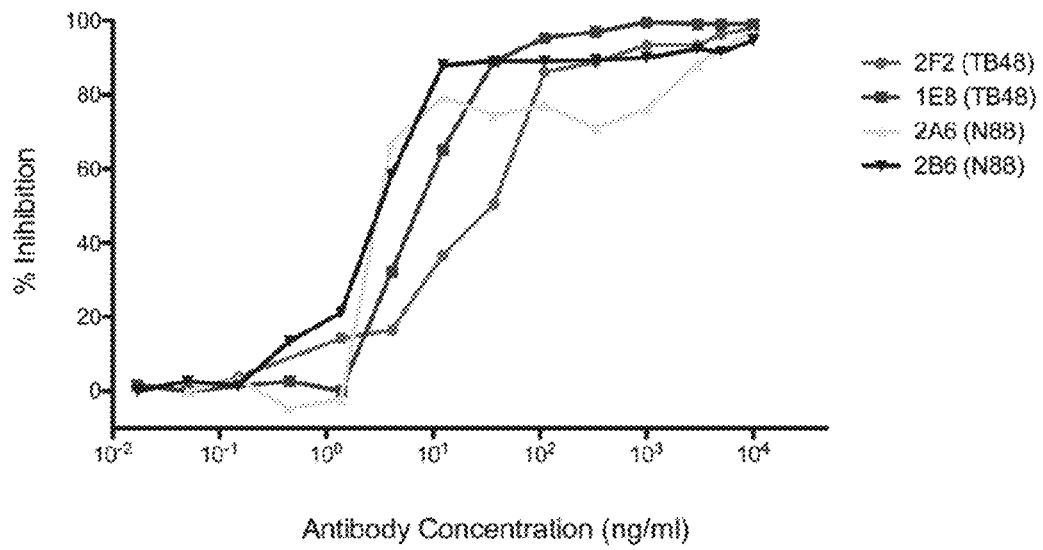
FIG. 5 shows IFN-γ induced HLA-DR expression can be dose dependently and effectively inhibited by antibodies in this disclosure.

FIG. 5 shows IFN-γ induced HLA-DR expression can be dose dependently and effectively inhibited by antibodies in present disclosure. It can be seen from FIG. 5 that, the inhibition percentage increased when the concentrations of each of the 2A6, 2B6, 1E8, and 2F2 anti-IFN-γ antibodies increased.

The $IC_{50}$ (ng/mL) of 2F2, 1E8, 2A6, and 2B6 anti-IFN-γ antibodies were 36.1, 8.6, 3.4, and 3.5, respectively. The $IC_{90}$ (ng/mL) of 2F2, 1E8, 2A6, and 2B6 anti-IFN-γ antibodies were 507.7, 48.6, 3851.3, and 1020.5, respectively. The above results indicated that the antibodies of the present disclosure can effectively inhibit IFN-γ mediated activity and could be used in the treatment of IFN-γ mediated syndromes.
C. ELISA Assay of Anti-IFN-γ Antibodies.

Figure 6:
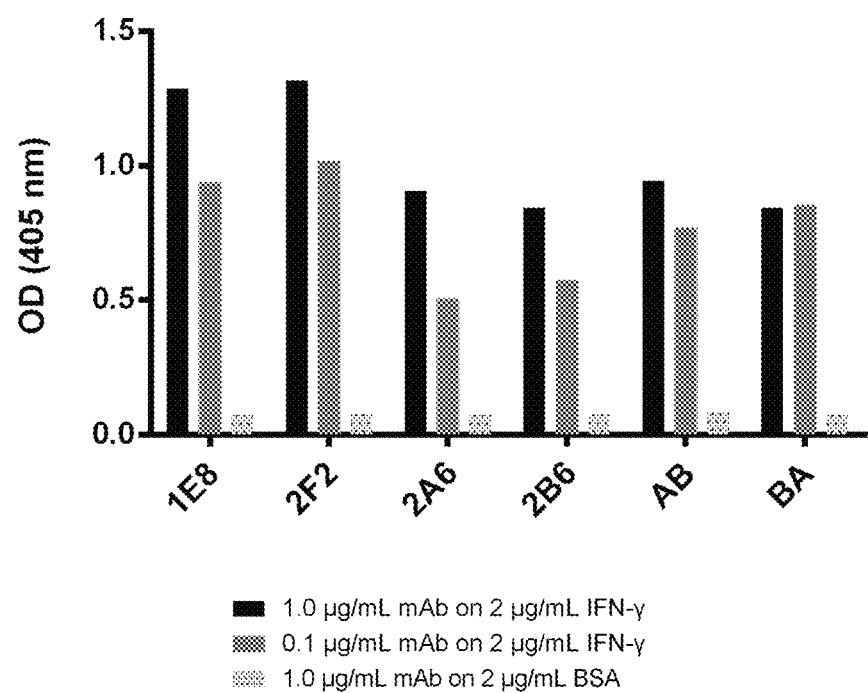
FIG. 6 shows the result of the ELISA in Example 2, representing the IFN-γ binding affinity of the antibodies of the present disclosure.

Absorbance of the plate wells as indicated by optical density at 405 nm ($OD_{405}$) for detection of human anti-IFN-γ antibody is shown in FIG. 6. It can be seen from FIG. 6 that the mAbs with the higher concentration (1 μg/mL) displayed stronger absorbance than those with the lower concentration (0.1 µg/mL). In addition, the mAbs were not bound to BSA, indicating that the antibodies of the present disclosure can specifically bind to human IFN-γ.

Example 3. Determination of the Activity of the Recombinant Anti-IFN-γ Antibodies In this example, antibodies 2A6, 2A6_A, 2A6_Q, 2B6, AB and BA of the present disclosure were tested for their binding affinity (ELISA) and neutralizing activity (cell-based assay and whole blood assay) with IFN-γ. Besides, AMG811 was also used as a positive control and comparative example.

A. ELISA Assay of Anti-IFN-γ Antibody Using Biotinylated IFN-γ.

Recombinant human IFN-γ (R&D systems 285-IF-100) and Cynomolgus IFN-γ (R&D systems 961-RM-025) were biotinylated according to kit manual (EZ-Link NHS-LC-Biotin; Thermo #21336) and bound to streptavidin coated plate respectively. After incubated at room temperature for 1-2 hours, the plate was washed three times with 300 µL wash buffer. Serial dilutions of anti-IFN-γ antibody were added to wells. After incubated at room temperature for 1-2 hours, the plate was washed three times with 300 µL wash buffer. HRP anti-Human IgG was applied to each well at room temperature for 1 hour incubation. After washing, the plates were developed with TMB substrate, and analyzed under $OD_{450-650}$.

Figure 7:
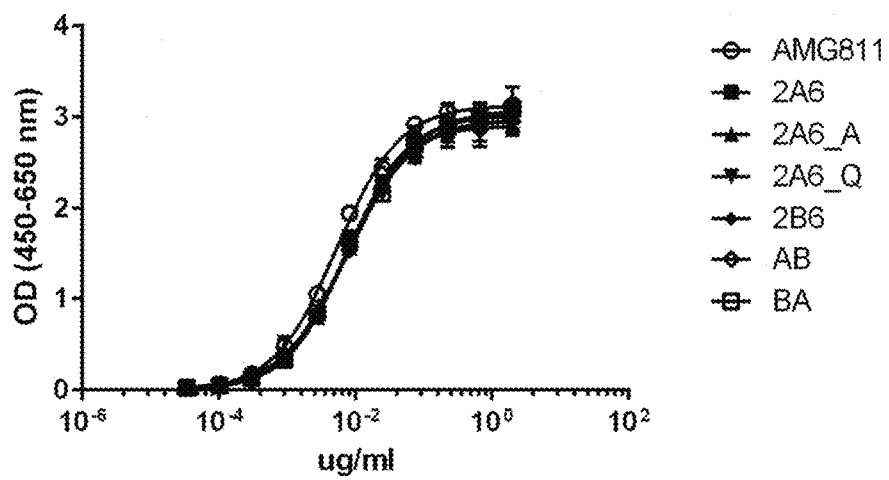
FIG. 7 shows the result of the ELISA in Example 3, representing the human IFN-γ (R&D systems 285-IF-100) binding affinity of the antibodies of the present disclosure.
Figure 8:
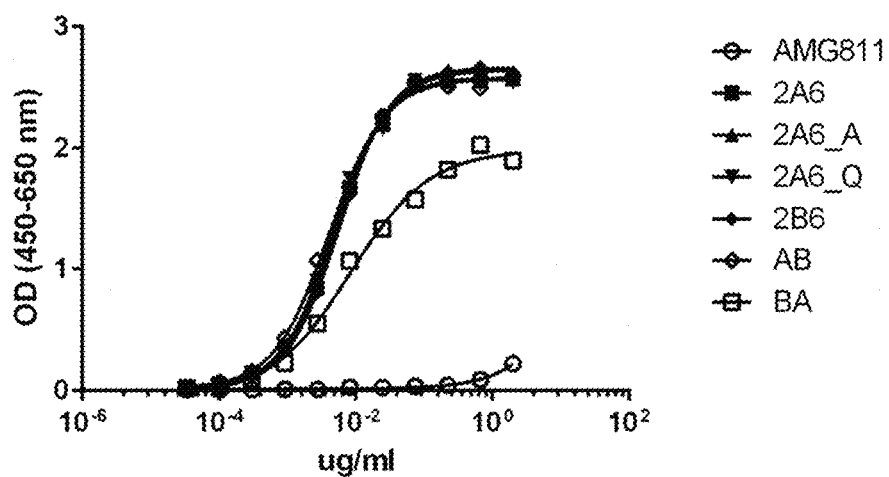
FIG. 8 shows the result of the ELISA in Example 3, representing the rhesus macaque/cynomolgus IFN-γ (R&D systems 961-RM-025) binding affinity of the antibodies of the present disclosure.

The results were shown in FIG. 7 and FIG. 8. It was noted that all the tested anti-IFN-γ antibodies of the present disclosure exhibited good binding affinity with human IFN-γ. Moreover, their binding affinity showed no significant difference from theAMG811's affinity (FIG. 7). The tested anti-IFN-γ antibodies of the present disclosure also exhibited cross-reactivity with rhesus macaque/cynomolgus IFN-γ although their affinity to human IFN-γ was higher. It was notable that AMG811 did not show the cross-reactivity exhibited by the anti-IFN-γ antibodies of the present disclosure (FIG. 8)—a significant advantage of the antibodies of the present disclosure.

B. Cell-Based Assay of Anti-IFN-γ Antibody.

A Luciferase Reporter HeLa Stable Cell Line expressing pGL4[luc2P/GAS-RE/Hygro (Promega #CS179301) was used to measure neutralizing activity of anti-IFN-γ antibody. Briefly, HeLa cell line was plated in 96-well white plates at $8 \times 10^3$ cells/well. Cells were treated with 1 ng/ml IFN-γ and different concentrations of anti-IFN-γ antibody for 18 h. Luciferase activity was analyzed using ONE-Glo™ Luciferase Assay System (Promega #E6110).

Figure 9:
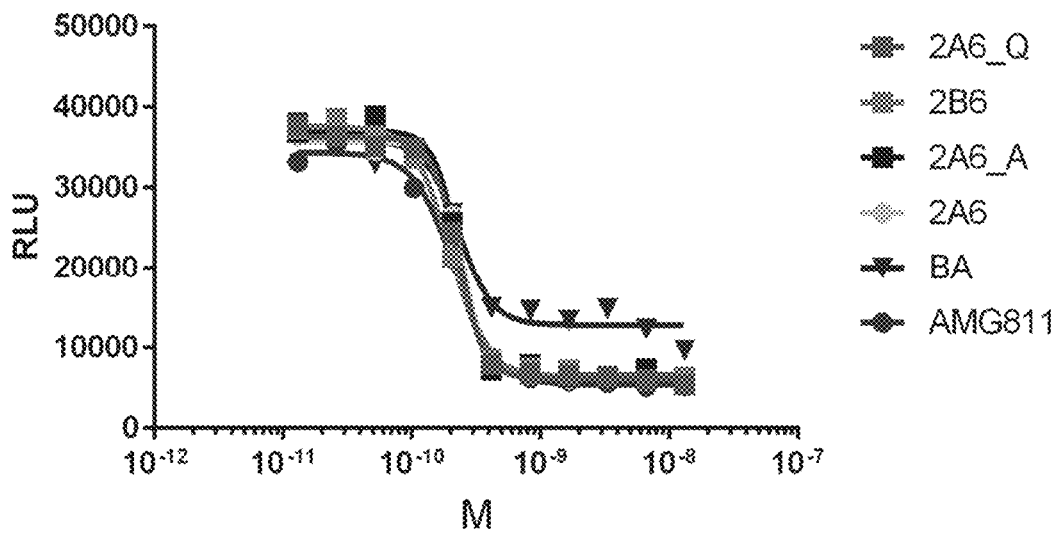
FIG. 9 exhibits the neutralizing activities of the antibodies of the present disclosure to IFN-γ.

The result shows that all tested antibodies were able to neutralize the activity of IFN-γ (FIG. 9). All antibodies tested were considered having sufficient neutralizing activity for industrial or pharmaceutical application.

C. Whole Blood Assay of Anti-IFN-γ Antibody.

Whole blood from healthy volunteers who had been vaccinated with bacillus Calmette-Guérin (BCG) was collected in 10-ml heparinized tubes. 20-µl samples of whole blood were added to 80 µl of RPMI 1640 culture medium with or without BCG+IL12 (20 ng/ml) in round-bottom wells of a 96-well microtiter plate. The microtiter plate was incubated at 37° C., 5% $CO_2$ for 48 h. Following incubation, CXCL9 was measured using CXCL9 ELISA kit (R&D systems DCX900). CXCL10 was measured using CXCL10 ELISA kit (Biolegend 439905). Cytokine levels were presented after correction with the dilution factor. Human IgG1 isotype control was used in the experiment as a negative control.

As expected, human whole blood samples produce high level of IFN-γ, and CXCL9 as well as CXCL10, whose productions are known to be regulated by IFN-γ. Inhibition of endogenous IFN-γ would block IFN-γ-dependent production of CXCL9 and CXCL10.

Figure 10:
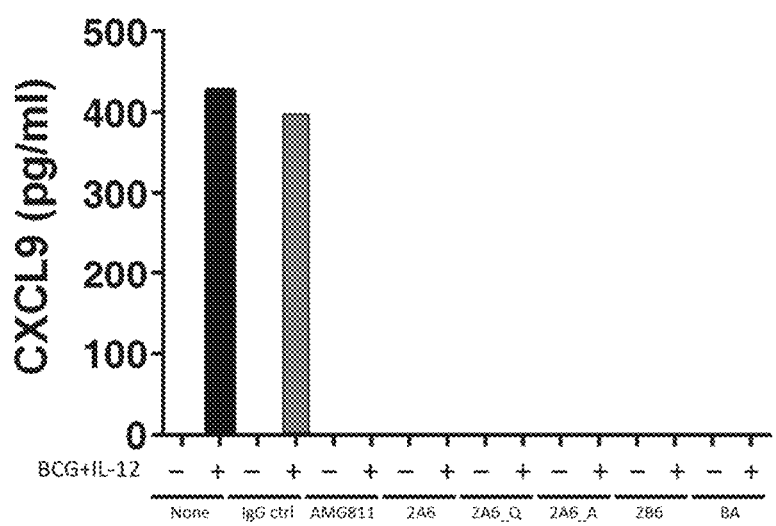
FIG. 10 shows the inhibition of CXCL9 production in the whole blood assay of anti-IFN-γ antibody conducted in Example 3.
Figure 11:
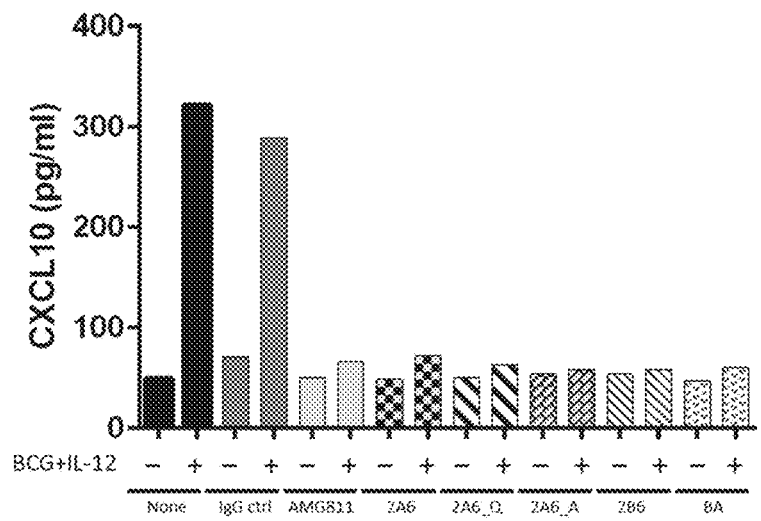
FIG. 11 shows the inhibition of CXCL10 production in the whole blood assay of anti-IFN-γ antibody conducted in Example 3.

The result verified that the anti-IFN-γ antibodies of the present disclosure effectively inhibited CXCL9 and CXCL10 production by neutralizing endogenous IFN-γ (FIG. 10 and FIG. 11).

D. Inhibition of T Cell Inhibitory Receptor Ligands by Anti-IFN-γ Antibody.

THP-1 cells were cultured according to ATCC instructions. For neutralizing assay, 40 ng/ml IFN-γ in 500 µl of RPMI-1640 was incubated with different amounts of anti-IFN-γ antibodies for 10 mins, and the mixture was added to $4 \times 10^5$ cells (500 µl). The final concentrations of IFN-γ antibodies were 0, 40, 200 or 1000 ng/ml. After incubation for 72 hrs in an incubator at 37° C., cells were stained with PE anti-human PD-L1 Antibody (Biolegend 329706) or FITC anti-human HLA-DR Antibody (Biolegend 327006) and incubated for 30 mins on ice in the dark. The cells were washed with 2 ml of FACS buffer twice and resuspended in 300 µl of FACS buffer. Data were acquired with a FACSCalibur flow cytometer.

Figure 12:
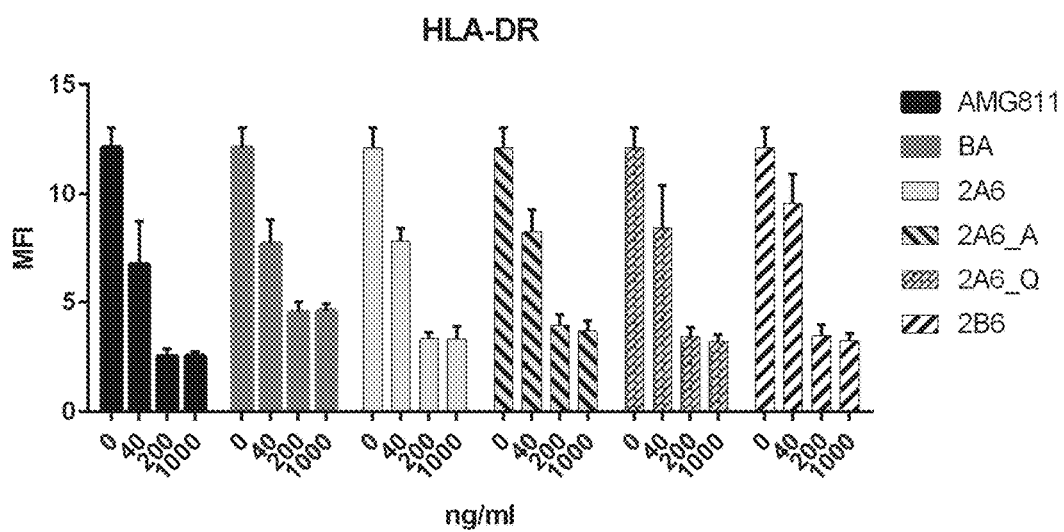
FIG. 12 illustrates the inhibitory effect of the antibodies of the present disclosure on IFN-γ-induced expression of HLA-DR.
Figure 13:
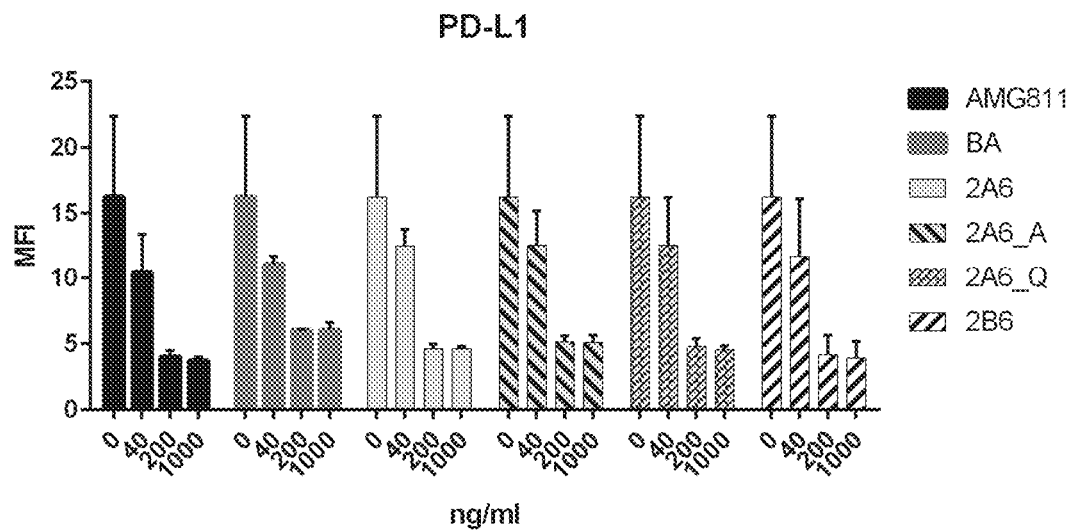
FIG. 13 illustrates the inhibitory effect of the antibodies of the present disclosure on IFN-γ-induced expression of PD-L1.

The results confirmed the anti-IFN-γ antibodies of the present disclosure were able to inhibit IFN-γ-induced expression of HLA-DR (FIG. 12) and PD-L1 (FIG. 13) in a dose dependent pattern. Together with the data in the cell-based assay and whole blood assay above, the antibodies of the present disclosure not only showed binding affinity with IFN-γ but also are capable to inhibit the activities of IFN-γ.

Example 4. Epitope Determination of the Antibodies of the Present Disclosure

A. Epitope Binning Experiments.

Epitope binning experiments was conducted to determine which anti-IFN-γ antibodies compete for binding to IFN-γ, and thus, bind to the same or similar epitopes of IFN-γ. Briefly, Strepavidin-coated Octet biosensor tips (FortéBio) were used to study the epitope in a set of four anti-IFN-γ antibodies of the present disclosure: 1E8, 2F2, 2A6 and 2B6. In the beginning, 2 µg/mL of biotinylated recombinant human IFN-γ was loaded onto streptavidin sensor tips to acquire 0.5 nm shift. Following 100 stable and 120 sec baseline steps, the primary anti-IFN-γ antibodies were individually loaded in an association step for 600 sec onto the tips at 5 µg/mL. Further, the secondary anti-IFN-γ antibodies also incubated with biosensor tips for 600 sec association at 5 µg/mL. If the signal showed mass accumulation to the tips, it was considered to bind to a different epitope.

Figure 14:
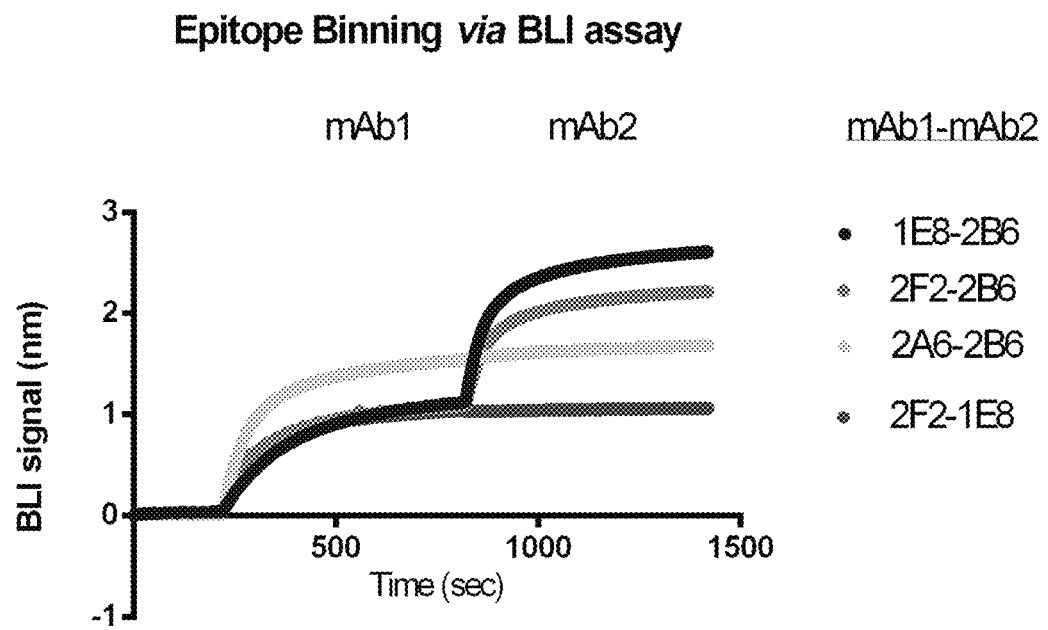
FIG. 14 shows the results of the epitope binning experiments conducted in Example 4.

Results of the epitope binning experiments for four of the anti-IFN-γ antibodies of the present disclosure, 2A6, 2B6, 1E8, and 2F2 are provided at FIG. 14. These four anti-IFN-γ antibodies fall into two epitope groups: Group I, comprising 1E8 and 2F2; and Group II comprising 2A6 and 2B6. In other words, 1E8 and 2F2 have a similar/same IFN-γ epitope, and 2A6 and 2B6 have similar/same IFN-γ epitope.

B. Mapping of the Epitope on Human IFN-γ Using HDX.

The hydrogen-deuterium exchange (HDX) in IFN-γ was measured by pepsin-digested fragments using HDX MS method in the presence and absence of the anti-IFN-γ antibody. The recombinant protein (15 pmol) and protein-antibody complex (15 pmol:10 pmol) were diluted in the exchange buffer (99.9% D20 in PBS, pH 7.4) at 1:10 ratio to initiate HD exchange at room temperature. At 7 time points (10s, 40s, 80s, 180s, 600s, 1800s, 3600s), an aliquot (1.5 pmol of target protein) was aspired and mixed with prechilled quenching buffer (to a final concentration of 1.5 M guanidine hydrochloride, 150 mM tris (2-carboxyethyl) phosphine, and 0.8% formic acid). The mixture was analyzed in an Orbitrap mass spectrometer. MS and MS/MS automatic gain control were set to 1,000 ms (full scan) and 120 ms (MS/MS), or $2 \times 10^6$ ions (full scan) and $3 \times 10^3$ ions (MS/MS) for maximum accumulated time or ions, respectively. Larger than 10% changes in average deuterium incorporation during the exchange time were considered significant in our analysis.

Based on the HDX-MS epitope mapping data, the proposed epitope on human IFN-γ for antibody 2A6_Q and antibody 2B6 comprises residues in two discontinuous amino acid segments: amino acids 30-52 and amino acids 78-92 of SEQ ID NO: 166. More specifically, the proposed epitope on human IFN-γ for antibody 2A6_Q and antibody 2B6 comprises residues in two discontinuous amino acid segments: amino acids 36-48 and amino acids 82-92 of SEQ ID NO: 166. The HDX epitopes for anti-IFN-γ antibodies 2A6_Q and 2B6 are provided at Table 7.

C. Alanine Scanning Mutagenesis.

Alanine scanning mutagenesis was used to identify specific residues in these regions that are important for binding Amino acids between 36-48 and 82-92 of SEQ ID NO: 166 were each mutated to alanine. Among all mutants, ten substitutions (residues 39, 41, 42, 44, 45, 47, 85, 88, 91, 92) reduced the biological activity of IFN-γ (determined using HeLa Stable Cell Line expressing pGL4[luc2P/GAS-RE/Hygro (Promega #CS179301)] and were therefor excluded from ELISA assay due to possible conformation change as a result of alanine substitution.

ELISA binding of 2A6_Q or 2B6 to the rest of IFN-γ mutant proteins was compared to wild-type IFN-γ. Mutations that reduce binding as evidenced by a reduction in maximum ELISA binding signal to 20% or less of wildtype were considered to significantly influence binding between IFN-γ and antibody. The results are shown in Table 7. The binding assay data are in good agreement with the binding region as mapped by HDX MS.

Furthermore, data from HDX analysis was plotted as Time vs. Reduced H Exchange. Analysis of these data plots together with the MS data indicated that the antibodies bound to a discontinuous epitope comprising at least amino acids 36-48 and 82-92 of SEQ ID NO: 166. HDX analysis of longer regions indicated that the epitope likely extends further and comprises the discontinuous amino acids 30-52 and 78-92 of the IFN-γ sequence of SEQ ID NO: 166.

In light of the foregoing, it is concluded that antibodies 2A6, 2B6 and 2A6_Q recognized K37, E38, K43, Q46, Q48, K86, and R89 of IFN-γ (SEQ ID NO: 166) and showed stronger binding affinity to K43, Q48, and K86 of IFN-γ (SEQ ID NO: 166).

TABLE 7

| 2A6_Q | Region 1 | Region 2 |
| --- | --- | --- |
| HDX | Amino acids 30-52 or amino acids 36-48 | Amino acids 78-92 or amino acids 82-92 |
| Alanine scanning Reduce >20% binding | K37, E38, K43, Q46, Q48 | K86, R89 |
| Alanine scanning Reduce >50% binding | K43, Q48 | K86 |
| 2B6 | Region 1 | Region 2 |
| HDX | Amino acids 30-52 or amino acids 36-48 | Amino acids 78-92 or amino acids 82-92 |
| Alanine scanning Reduce >20% binding | K37, E38, K43, Q46, Q48 | K86, R89 |
| Alanine scanning Reduce >50% binding | K43, Q48 | K86 |

Primer listing.

| | 5'-3' sequence | SEQ ID No. |
| --- | --- | --- |
| Forward primer | | |
| VH1/7L | accatggactgsacctggag | 1 |
| VH2L | caccatggacacactttgctmcac | 2 |
| VH2-70L | accatggacatactttgttccacg | 3 |
| VH3L | atggagtttgggctgagctg | 4 |
| VH3-21L | atggaactggggctccgctg | 5 |
| VH3-48L | atggagttggggctgtgctg | 6 |
| VH3-49L | catggagtttgggcttagctg | 7 |
| VH3-53L | catggagttttggctgagctg | 8 |
| VH4L | catgaaacacctgtggttcttcct | 9 |
| VH4-39L | aatgaagcacctgtggttcttcct | 10 |
| VH4-59L | acatgaaacatctgtggttcttcct | 11 |
| VH5L | atggggtcaaccgccatcct | 12 |
| VH6L | aatgtctgtctccttcctcatcttcct | 13 |
| VH1/3/5f | saggtgcagctggtgsagtc | 14 |
| VH1-3f | caggtccagcttgtgcagtc | 15 |
| VH1-18f | caggttcagctggtgcagtc | 16 |
| VH1-24f | caggtccagctggtacagtctg | 17 |
| VH2f | caggtcacctgargagtctggt | 18 |
| VH3-23f | gaggtgcagctgttggagtct | 19 |
| VH4f | cagstgcagctgcaggagt | 20 |
| VH4-34f | caggtgcagctacarcagtgg | 21 |
| VH6f | caggtacagctgcagcagtca | 22 |
| VH7f | caggtgcagctggtgcaat | 23 |
| KV1L | ggtccccgctcagctcctgg | 24 |
| KV1-16L | agtcctcgctcagctcctgg | 25 |
| V2L | gctccctgctcagctcctgg | 26 |
| KV2-24L | gctccttgctcagcttctgg | 27 |

-continued

Primer listing.

| | 5'-3' sequence | SEQ ID No. |
|---|---|---|
| KV3L | cctgctactctggctcccag | 28 |
| KV4L | atttctctgttgctctggatctctg | 29 |
| KV5L | cacctcctcctaggatctctg | 30 |
| KV6L | tctgctgctctgggttccag | 31 |
| VK1f | gacatccagwtgacccagtctcc | 32 |
| VK2f | gatattgtgatgacccagactccactct | 33 |
| VK2-28f | gatattgtgatgactcagtctccactct | 34 |
| VK3f | gaaattgtgttgacrcagtctccag | 35 |
| VK3-15f | gaaatagtgatgacgcagtctccag | 36 |
| VK4f | gacatcgtgatgacccagtctc | 37 |
| VK5f | gaaacgacactcacgcagtctc | 38 |
| VK6f | gaaattgtgctgactcagtctcca | 39 |
| LV1L | ggtcctgggcccagtctgtg | 40 |
| LV2L | ggtcctgggcycagtctgcc | 41 |
| LV3L | gctctgwggcctcctatgagct | 42 |
| LV3-12/21L | gctctgtgacctcctatgwgctg | 43 |
| LV3-19L | gttctgtggtttcttctgagctgact | 44 |
| LV4L | ggtctctctcccwgcytgtgc | 45 |
| LV5L | gttccctctcgcaggctgtg | 46 |
| LV5/9L | gktccctctcccagcctgtg | 47 |
| LV6L | gttcttgggccaattttatgctg | 48 |
| LV7L | ggtccaattcycagrctgtggtg | 49 |
| LV8L | gagtggattctcagactgtggtga | 50 |
| LV10L | tgtcagtggtccaggcaggg | 51 |
| LV1-40/50/51f | cagtctgtgytgacgcagcc | 52 |
| LV1-36/44/47f | cagtctgtgctgactcagcca | 53 |
| LV2f | cagtctgccctgactcagcc | 54 |
| LV3f | tcctatgagctgacwcagcca | 55 |
| LV3-19f | tcttctgagctgactcaggacc | 56 |
| LV4/5/9f | cagsctgtgctgactcagcc | 57 |
| LV4-60f | cagcctgtgctgactcaatcat | 58 |
| LV4-69f | cagcttgtgctgactcaatcg | 59 |
| LV6f | aattttatgctgactcagccccac | 60 |
| LV7/8f | cagrctgtggtgacycaggagc | 61 |
| LV10f | caggcagggctgactcagcc | 62 |

Reverse primers

| CγCH1-1 | aggtgtgcacgccgctggtc | 63 |
| CγCH1-2 | ggttcggggaagtagtccttgac | 64 |
| Cκ543-566 | gttttctcgtagtctgctttgctca | 65 |
| Cκ494-516 | gtgctgtccttgctgtcctgct | 66 |
| Cλ156-178 | ttggagggtktggtggtctccac | 67 |
| Cλ129-148 | ttgacggggctgcyatctgc | 68 |
| Cλ93-113 | cacrgctcccgggtagaagtc | 69 |

Primer

| SL-VH1/3/5f | gttgctacgcgtgtcctgagcsaggtgcagctggtgsagtc | 70 |
| SL-VH1-3f | gttgctacgcgtgtcctgagccaggtccagcttgtgcagtc | 71 |
| SL-VH1-18f | gttgctacgcgtgtcctgagccaggttcagctggtgcagtc | 72 |
| SL-VH1-24f | gttgctacgcgtgtcctgagccaggtccagctggtacagtctg | 73 |
| SL-VH2f | gttgctacgcgtgtcctgagccaggtcaccttgarggagtctg | 74 |
| SL-VH3-23f | gttgctacgcgtgtcctgagcgaggtgcagctgttggagtct | 75 |
| SL-VH4f | gttgctacgcgtgtcctgagccagstgcagctgcaggagt | 76 |
| SL-VH4-34f | gttgctacgcgtgtcctgagccaggtgcagctacarcagtgg | 77 |
| SL-VH6f | gttgctacgcgtgtcctgagccaggtacagctgcagcagtca | 78 |
| SL-VH7f | gttgctacgcgtgtcctgagccaggtgcagctggtgcaat | 79 |
| SL-JH1/4/5r | gatgggcccttggtgctagctgaggagacggtgaccagg | 80 |
| SL-JH2r | gatgggcccttggtgctagctgaggagacagtgaccagggt | 81 |
| SL-JH3r | gatgggcccttggtgctagctgaagagacggtgaccattgtc | 82 |
| SL-JH6r | gatgggcccttggtgctagctgaggagacggtgaccgtg | 83 |
| SL-VK1f | ggctcccaggtgcacgatgtgacatccagwtgacccagtctcc | 84 |
| SL-VK2f | ggctcccaggtgcacgatgtgatattgtgatgacccagactccactct | 85 |
| SL-VK3f | ggctcccaggtgcacgatgtgaaattgtgttgacrcagtctccag | 86 |
| SL-VK4f | ggctcccaggtgcacgatgtgacatcgtgatgacccagtctc | 87 |
| SL-VK5f | ggctcccaggtgcacgatgtgaaacgacactcacgcagtctc | 88 |
| SL-VK6f | ggctcccaggtgcacgatgtgaaattgtgctgactcagtctcca | 89 |
| SL-JK1r | tgcagccaccgtacgtttgatttccaccttggtccct | 90 |
| SL-JK2r | tgcagccaccgtacgtttgatctccagcttggtccct | 91 |
| SL-JK3r | tgcagccaccgtacgtttgatatccactttggtccca | 92 |
| SL-JK4r | tgcagccaccgtacgtttgatctccaccttggtccct | 93 |
| SL-JK5r | tgcagccaccgtacgtttaatctccagtcgtgtccctt | 94 |
| SL-LV1-40/50/51f | tc cttgcttatgggtccggagtggattctcagtctgtgytgacgcagcc | 95 |

| | Primer listing. | |
|---|---|---|
| | 5'-3' sequence | SEQ ID No. |
| SL-LV1-36/44/47f | tc cttgcttatgggtccggagtggattctcagtctgtgctgactcagcca | 96 |
| SL-LV2f | tc cttgcttatgggtccggagtggattctcagtctgccctgactcagcc | 97 |
| SL-LV3f | tc cttgcttatgggtccggagtggattcttcctatgagctgacwcagcca | 98 |
| SL-LV3-19f | tc cttgcttatgggtccggagtggattcttcttctgagctgactcaggac | 99 |
| SL-LV4/5/9f | tc cttgcttatgggtccggagtggattctcagsctgtgctgactcagcc | 100 |
| SL-LV4-60/69f | tc cttgcttatgggtccggagtggattctcagyctgtgctgactcaatc | 101 |
| SL-LV6f | tc cttgcttatgggtccggagtggattctaattttatgctgactcagccc | 102 |
| SL-LV7/8f | tccttgcttatgggtccggagtggattctcagrctgtggtgacycaggag | 103 |
| SL-LV10f | tccttgcttatgggtccggagtggattctcaggcagggctgactcagcc | 104 |
| SL-JL1r | ggccttgggctgacctaggacggtgaccttggtcc | 105 |
| SL-JL2/3f | ggccttgggctgacctaggacggtcagcttggtcc | 106 |
| SL-JL6r | ggccttgggctgacctaggacggtcaccttggtgc | 107 |
| SL-JL7r | ggccttgggctgacctaggacggtcagctgggtgc | 108 |
| pIgG₁κ-screen+ | gctcccaggtgcacgatgtg | 117 |
| pIgG₁λ-screen+ | gcttatgggtccggagtggattct | 118 |
| pIgG₁-screen- | gatgggcccttggtgctagc | 119 |

In connection with the Sequence Listing submitted concurrently herewith, the applicant hereby states that the content of the electronically filed submission is in accordance with 37 C.F.R. § 1.821(e), and the submission, in accordance with 7 C.F.R. § 1.821(g), does not include new matter.

What is claimed is:

1. An engineered antibody comprising:
V$_H$ CDR1, V$_H$ CDR2, V$_H$ CDR3, V$_L$ CDR1, V$_L$ CDR2, and V$_L$ CDR3, wherein
said V$_H$ CDR1, V$_H$ CDR2, and V$_H$ CDR3 are SEQ ID NO: 126, SEQ ID NO: 127, and SEQ ID NO: 128, respectively; wherein said V$_L$ CDR1, V$_L$ CDR2, V$_L$ CDR3 are SEQ ID NO: 138, SEQ ID NO: 139, and SEQ ID NO: 140, respectively;
said V$_H$ CDR1, V$_H$ CDR2, and V$_H$ CDR3 are SEQ ID NO: 150, SEQ ID NO: 151, and SEQ ID NO: 152, respectively; wherein said V$_L$ CDR1, V$_L$ CDR2, V$_L$ CDR3 are SEQ ID NO: 160, SEQ ID NO: 161, and SEQ ID NO: 140, respectively;
said V$_H$ CDR1, V$_H$ CDR2, and V$_H$ CDR3 are SEQ ID NO: 129, SEQ ID NO: 130, and SEQ ID NO: 131, respectively; wherein said V$_L$ CDR1, V$_L$ CDR2, V$_L$ CDR3 are SEQ ID NO: 141, SEQ ID NO: 142, and SEQ ID NO: 143, respectively; or
said V$_H$ CDR1, V$_H$ CDR2, and V$_H$ CDR3 are SEQ ID NO: 153, SEQ ID NO: 154, and SEQ ID NO: 155, respectively; wherein said V$_L$ CDR1, V$_L$ CDR2, V$_L$ CDR3 are SEQ ID NO: 162, SEQ ID NO: 163, and SEQ ID NO: 143, respectively;

wherein V$_H$ does not comprise an N-linked Glycosylation site.

2. The engineered antibody of claim 1, wherein V$_H$ comprises a sequence having at least 90% identity to SEQ ID NO: 111, or 112; and V$_L$ comprises a sequence having at least 90% identity to SEQ ID NO: 115, or 116 and wherein (a) V$_H$ CDR1, V$_H$ CDR2, and V$_H$ CDR3 are SEQ ID NO: 126, SEQ ID NO: 127, and SEQ ID NO: 128, respectively; and V$_L$ CDR1, V$_L$ CDR2, and V$_L$ CDR3 are SEQ ID NO: 138, SEQ ID NO: 139, and SEQ ID NO: 140, respectively;

(b) V$_H$ CDR1, V$_H$ CDR2, and V$_H$ CDR3 are SEQ ID NO: 150, SEQ ID NO: 151, and SEQ ID NO: 152, respectively; and V$_L$ CDR1, V$_L$ CDR2, and V$_L$ CDR3 are SEQ ID NO: 160, SEQ ID NO: 161, and SEQ ID NO: 140, respectively;

(c) V$_H$ CDR1, V$_H$ CDR2, and V$_H$ CDR3 are SEQ ID NO: 129, SEQ ID NO: 130, and SEQ ID NO: 131, respectively; and V$_L$ CDR1, V$_L$ CDR2, and V$_L$ CDR3 are SEQ ID NO: 141, SEQ ID NO: 142, and SEQ ID NO: 143, respectively; or (d) V$_H$ CDR1, V$_H$ CDR2, and V$_H$ CDR3 are SEQ ID NO: 153, SEQ ID NO: 154, and SEQ ID NO: 155, respectively; and $V_L$ CDR1, $V_L$ CDR2, and $V_L$ CDR3 are SEQ ID NO: 162, SEQ ID NO: 163, and SEQ ID NO: 143, respectively.

3. The engineered antibody of claim 2, wherein the antibody is a chimeric antibody, or a human antibody.

4. The engineered antibody of claim 2, wherein the antibody cross-reacts with IFN-γ from human, rhesus macaque and/or cynomolgus monkey.

5. The engineered antibody of claim 2, wherein said isolated antibody specifically binds human IFN-γ with a binding value $K_D$, measured by bio-layer interferometry analysis, of less than $1\times10^{-8}$ M.

6. The engineered antibody of claim 2, wherein the antibody inhibits human IFN-γ mediated activity with an $IC_{50}$ value, measured by HLA-DR expression analysis, of less than 50 ng/mL.

7. A vector comprising a polynucleotide encoding the engineered antibody of claim 1.

8. A host cell comprising the vector of claim 7.

9. A host cell expressing the engineered antibody of claim 1.

10. The host cell of claim 9, wherein the host cell is selected from the group consisting of *E. coli*, insect, yeast, or mammalian cells.

11. A pharmaceutical composition for neutralizing an activity of interferon-γ, comprising:

the engineered antibody of claim 1; and a pharmaceutically acceptable carrier.

12. A method for detecting interferon-γ in an environment, comprising:

(a) applying the engineered antibody of claim 1 into said environment;

(b) incubating said environment with an anti-IgG antibody conjugated with a detectable label; and (c) detecting said detectable label.

13. The method of claim 12, wherein the detectable label comprises an alkaline phosphatase; and the method further comprises incubating said environment with a p-nitrophenyl phosphate solution after step (b) and before step (c).

14. The method of claim 13, wherein said detecting of step (c) is conducted by determining the absorbance of said environment at $OD_{405}$.

* * * * *

SEQUENCE LISTING

<160> NUMBER OF SEQ ID NOS: 182

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
accatggact gsacctggag                                              20

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
caccatggac acactttgct mcac                                         24

<210> SEQ ID NO 3
<211> LENGTH: 24
<212> TYPE: DNA
<213> ORGANISM: Artificial Sequence
<220> FEATURE:
<223> OTHER INFORMATION: PRIMER

<400> SEQUENCE: 3
accatggaca tactttgttc cacg                                         24

<210> SEQ ID NO 4
<211> LENGTH: 20
<212> TYPE: DNA
<213> ORGANISM: Artificial Sequence
<220> FEATURE:
<223> OTHER INFORMATION: PRIMER

<400> SEQUENCE: 4
atggagtttg ggctgagctg                                                    20

<210> SEQ ID NO 5
<211> LENGTH: 20
<212> TYPE: DNA
<213> ORGANISM: Artificial Sequence
<220> FEATURE:
<223> OTHER INFORMATION: PRIMER

<400> SEQUENCE: 5
atggaactgg ggctccgctg                                                    20

<210> SEQ ID NO 6
<211> LENGTH: 20
<212> TYPE: DNA
<213> ORGANISM: Artificial Sequence
<220> FEATURE:
<223> OTHER INFORMATION: PRIMER

<400> SEQUENCE: 6
atggagttgg ggctgtgctg                                                    20

<210> SEQ ID NO 7
<211> LENGTH: 21
<212> TYPE: DNA
<213> ORGANISM: Artificial Sequence
<220> FEATURE:
<223> OTHER INFORMATION: PRIMER

<400> SEQUENCE: 7
catggagttt gggcttagct g                                                  21

<210> SEQ ID NO 8
<211> LENGTH: 21
<212> TYPE: DNA
<213> ORGANISM: Artificial Sequence
<220> FEATURE:
<223> OTHER INFORMATION: PRIMER

<400> SEQUENCE: 8
catggagttt tggctgagct g                                                  21

<210> SEQ ID NO 9
<211> LENGTH: 24
<212> TYPE: DNA
<213> ORGANISM: Artificial Sequence
<220> FEATURE:
<223> OTHER INFORMATION: PRIMER

<400> SEQUENCE: 9
catgaaacac ctgtggttct tcct                                               24

<210> SEQ ID NO 10
<211> LENGTH: 24
<212> TYPE: DNA
<213> ORGANISM: Artificial Sequence
<220> FEATURE:
<223> OTHER INFORMATION: PRIMER

<400> SEQUENCE: 10
aatgaagcac ctgtggttct tcct                                               24

<210> SEQ ID NO 11
<211> LENGTH: 25
<212> TYPE: DNA
<213> ORGANISM: Artificial Sequence

```
<220> FEATURE:
<223> OTHER INFORMATION: PRIMER

<400> SEQUENCE: 11
acatgaaaca tctgtggttc ttcct                                              25

<210> SEQ ID NO 12
<211> LENGTH: 20
<212> TYPE: DNA
<213> ORGANISM: Artificial Sequence
<220> FEATURE:
<223> OTHER INFORMATION: PRIMER

<400> SEQUENCE: 12
atggggtcaa ccgccatcct                                                    20

<210> SEQ ID NO 13
<211> LENGTH: 27
<212> TYPE: DNA
<213> ORGANISM: Artificial Sequence
<220> FEATURE:
<223> OTHER INFORMATION: PRIMER

<400> SEQUENCE: 13
aatgtctgtc tccttcctca tcttcct                                            27

<210> SEQ ID NO 14
<211> LENGTH: 20
<212> TYPE: DNA
<213> ORGANISM: Artificial Sequence
<220> FEATURE:
<223> OTHER INFORMATION: PRIMER

<400> SEQUENCE: 14
saggtgcagc tggtgsagtc                                                    20

<210> SEQ ID NO 15
<211> LENGTH: 20
<212> TYPE: DNA
<213> ORGANISM: Artificial Sequence
<220> FEATURE:
<223> OTHER INFORMATION: PRIMER

<400> SEQUENCE: 15
caggtccagc ttgtgcagtc                                                    20

<210> SEQ ID NO 16
<211> LENGTH: 20
<212> TYPE: DNA
<213> ORGANISM: Artificial Sequence
<220> FEATURE:
<223> OTHER INFORMATION: PRIMER

<400> SEQUENCE: 16
caggttcagc tggtgcagtc                                                    20

<210> SEQ ID NO 17
<211> LENGTH: 22
<212> TYPE: DNA
<213> ORGANISM: Artificial Sequence
<220> FEATURE:
<223> OTHER INFORMATION: PRIMER

<400> SEQUENCE: 17
caggtccagc tggtacagtc tg                                                 22
```

```
<210> SEQ ID NO 18
<211> LENGTH: 23
<212> TYPE: DNA
<213> ORGANISM: Artificial Sequence
<220> FEATURE:
<223> OTHER INFORMATION: PRIMER

<400> SEQUENCE: 18
caggtcacct garggagtct ggt                                              23

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gaggtgcagc tgttggagtc t                                                21

<210> SEQ ID NO 20
<211> LENGTH: 19
<212> TYPE: DNA
<213> ORGANISM: Artificial Sequence
<220> FEATURE:
<223> OTHER INFORMATION: PRIMER

<400> SEQUENCE: 20
cagstgcagc tgcaggagt                                                   19

<210> SEQ ID NO 21
<211> LENGTH: 21
<212> TYPE: DNA
<213> ORGANISM: Artificial Sequence
<220> FEATURE:
<223> OTHER INFORMATION: PRIMER

<400> SEQUENCE: 21
caggtgcagc tacarcagtg g                                                21

<210> SEQ ID NO 22
<211> LENGTH: 21
<212> TYPE: DNA
<213> ORGANISM: Artificial Sequence
<220> FEATURE:
<223> OTHER INFORMATION: PRIMER

<400> SEQUENCE: 22
caggtacagc tgcagcagtc a                                                21

<210> SEQ ID NO 23
<211> LENGTH: 19
<212> TYPE: DNA
<213> ORGANISM: Artificial Sequence
<220> FEATURE:
<223> OTHER INFORMATION: PRIMER

<400> SEQUENCE: 23
caggtgcagc tggtgcaat                                                   19

<210> SEQ ID NO 24
<211> LENGTH: 20
<212> TYPE: DNA
<213> ORGANISM: Artificial Sequence
<220> FEATURE:
<223> OTHER INFORMATION: PRIMER
```

```
<400> SEQUENCE: 24
ggtccccgct cagctcctgg                                        20

<210> SEQ ID NO 25
<211> LENGTH: 20
<212> TYPE: DNA
<213> ORGANISM: Artificial Sequence
<220> FEATURE:
<223> OTHER INFORMATION: PRIMER

<400> SEQUENCE: 25
agtcctcgct cagctcctgg                                        20

<210> SEQ ID NO 26
<211> LENGTH: 20
<212> TYPE: DNA
<213> ORGANISM: Artificial Sequence
<220> FEATURE:
<223> OTHER INFORMATION: PRIMER

<400> SEQUENCE: 26
gctccctgct cagctcctgg                                        20

<210> SEQ ID NO 27
<211> LENGTH: 20
<212> TYPE: DNA
<213> ORGANISM: Artificial Sequence
<220> FEATURE:
<223> OTHER INFORMATION: PRIMER

<400> SEQUENCE: 27
gctccttgct cagcttctgg                                        20

<210> SEQ ID NO 28
<211> LENGTH: 20
<212> TYPE: DNA
<213> ORGANISM: Artificial Sequence
<220> FEATURE:
<223> OTHER INFORMATION: PRIMER

<400> SEQUENCE: 28
cctgctactc tggctcccag                                        20

<210> SEQ ID NO 29
<211> LENGTH: 25
<212> TYPE: DNA
<213> ORGANISM: Artificial Sequence
<220> FEATURE:
<223> OTHER INFORMATION: PRIMER

<400> SEQUENCE: 29
atttctctgt tgctctggat ctctg                                  25

<210> SEQ ID NO 30
<211> LENGTH: 23
<212> TYPE: DNA
<213> ORGANISM: Artificial Sequence
<220> FEATURE:
<223> OTHER INFORMATION: PRIMER

<400> SEQUENCE: 30
cttcctcctc ctttggatct ctg                                    23

<210> SEQ ID NO 31
```

<211> LENGTH: 20
<212> TYPE: DNA
<213> ORGANISM: Artificial Sequence
<220> FEATURE:
<223> OTHER INFORMATION: PRIMER

<400> SEQUENCE: 31
tctgctgctc tgggttccag                                               20

<210> SEQ ID NO 32
<211> LENGTH: 23
<212> TYPE: DNA
<213> ORGANISM: Artificial Sequence
<220> FEATURE:
<223> OTHER INFORMATION: PRIMER

<400> SEQUENCE: 32
gacatccagw tgacccagtc tcc                                           23

<210> SEQ ID NO 33
<211> LENGTH: 28
<212> TYPE: DNA
<213> ORGANISM: Artificial Sequence
<220> FEATURE:
<223> OTHER INFORMATION: PRIMER

<400> SEQUENCE: 33
gatattgtga tgacccagac tccactct                                      28

<210> SEQ ID NO 34
<211> LENGTH: 28
<212> TYPE: DNA
<213> ORGANISM: Artificial Sequence
<220> FEATURE:
<223> OTHER INFORMATION: PRIMER

<400> SEQUENCE: 34
gatattgtga tgactcagtc tccactct                                      28

<210> SEQ ID NO 35
<211> LENGTH: 25
<212> TYPE: DNA
<213> ORGANISM: Artificial Sequence
<220> FEATURE:
<223> OTHER INFORMATION: PRIMER

<400> SEQUENCE: 35
gaaattgtgt tgacrcagtc tccag                                         25

<210> SEQ ID NO 36
<211> LENGTH: 25
<212> TYPE: DNA
<213> ORGANISM: Artificial Sequence
<220> FEATURE:
<223> OTHER INFORMATION: PRIMER

<400> SEQUENCE: 36
gaaatagtga tgacgcagtc tccag                                         25

<210> SEQ ID NO 37
<211> LENGTH: 22
<212> TYPE: DNA
<213> ORGANISM: Artificial Sequence
<220> FEATURE:
<223> OTHER INFORMATION: PRIMER

<400> SEQUENCE: 37
gacatcgtga tgacccagtc tc                                              22

<210> SEQ ID NO 38
<211> LENGTH: 22
<212> TYPE: DNA
<213> ORGANISM: Artificial Sequence
<220> FEATURE:
<223> OTHER INFORMATION: PRIMER

<400> SEQUENCE: 38
gaaacgacac tcacgcagtc tc                                              22

<210> SEQ ID NO 39
<211> LENGTH: 24
<212> TYPE: DNA
<213> ORGANISM: Artificial Sequence
<220> FEATURE:
<223> OTHER INFORMATION: PRIMER

<400> SEQUENCE: 39
gaaattgtgc tgactcagtc tcca                                            24

<210> SEQ ID NO 40
<211> LENGTH: 20
<212> TYPE: DNA
<213> ORGANISM: Artificial Sequence
<220> FEATURE:
<223> OTHER INFORMATION: PRIMER

<400> SEQUENCE: 40
ggtcctgggc ccagtctgtg                                                 20

<210> SEQ ID NO 41
<211> LENGTH: 20
<212> TYPE: DNA
<213> ORGANISM: Artificial Sequence
<220> FEATURE:
<223> OTHER INFORMATION: PRIMER

<400> SEQUENCE: 41
ggtcctgggc ycagtctgcc                                                 20

<210> SEQ ID NO 42
<211> LENGTH: 22
<212> TYPE: DNA
<213> ORGANISM: Artificial Sequence
<220> FEATURE:
<223> OTHER INFORMATION: PRIMER

<400> SEQUENCE: 42
gctctgwggc ctcctatgag ct                                              22

<210> SEQ ID NO 43
<211> LENGTH: 23
<212> TYPE: DNA
<213> ORGANISM: Artificial Sequence
<220> FEATURE:
<223> OTHER INFORMATION: PRIMER

<400> SEQUENCE: 43
gctctgtgac ctcctatgwg ctg                                             23

<210> SEQ ID NO 44
<211> LENGTH: 26
<212> TYPE: DNA

```
<213> ORGANISM: Artificial Sequence
<220> FEATURE:
<223> OTHER INFORMATION: PRIMER

<400> SEQUENCE: 44
gttctgtggt tcttctgag ctgact                                              26

<210> SEQ ID NO 45
<211> LENGTH: 21
<212> TYPE: DNA
<213> ORGANISM: Artificial Sequence
<220> FEATURE:
<223> OTHER INFORMATION: PRIMER

<400> SEQUENCE: 45
ggtctctctc ccwgcytgtg c                                                  21

<210> SEQ ID NO 46
<211> LENGTH: 20
<212> TYPE: DNA
<213> ORGANISM: Artificial Sequence
<220> FEATURE:
<223> OTHER INFORMATION: PRIMER

<400> SEQUENCE: 46
gttccctctc gcaggctgtg                                                    20

<210> SEQ ID NO 47
<211> LENGTH: 20
<212> TYPE: DNA
<213> ORGANISM: Artificial Sequence
<220> FEATURE:
<223> OTHER INFORMATION: PRIMER

<400> SEQUENCE: 47
gktccctctc ccagcctgtg                                                    20

<210> SEQ ID NO 48
<211> LENGTH: 23
<212> TYPE: DNA
<213> ORGANISM: Artificial Sequence
<220> FEATURE:
<223> OTHER INFORMATION: PRIMER

<400> SEQUENCE: 48
gttcttgggc caattttatg ctg                                                23

<210> SEQ ID NO 49
<211> LENGTH: 23
<212> TYPE: DNA
<213> ORGANISM: Artificial Sequence
<220> FEATURE:
<223> OTHER INFORMATION: PRIMER

<400> SEQUENCE: 49
ggtccaattc ycagrctgtg gtg                                                23

<210> SEQ ID NO 50
<211> LENGTH: 24
<212> TYPE: DNA
<213> ORGANISM: Artificial Sequence
<220> FEATURE:
<223> OTHER INFORMATION: PRIMER

<400> SEQUENCE: 50
gagtggattc tcagactgtg gtga                                               24
```

<210> SEQ ID NO 51
<211> LENGTH: 20
<212> TYPE: DNA
<213> ORGANISM: Artificial Sequence
<220> FEATURE:
<223> OTHER INFORMATION: PRIMER

<400> SEQUENCE: 51
tgtcagtggt ccaggcaggg                                               20

<210> SEQ ID NO 52
<211> LENGTH: 20
<212> TYPE: DNA
<213> ORGANISM: Artificial Sequence
<220> FEATURE:
<223> OTHER INFORMATION: PRIMER

<400> SEQUENCE: 52
cagtctgtgy tgacgcagcc                                               20

<210> SEQ ID NO 53
<211> LENGTH: 21
<212> TYPE: DNA
<213> ORGANISM: Artificial Sequence
<220> FEATURE:
<223> OTHER INFORMATION: PRIMER

<400> SEQUENCE: 53
cagtctgtgc tgactcagcc a                                             21

<210> SEQ ID NO 54
<211> LENGTH: 20
<212> TYPE: DNA
<213> ORGANISM: Artificial Sequence
<220> FEATURE:
<223> OTHER INFORMATION: PRIMER

<400> SEQUENCE: 54
cagtctgccc tgactcagcc                                               20

<210> SEQ ID NO 55
<211> LENGTH: 21
<212> TYPE: DNA
<213> ORGANISM: Artificial Sequence
<220> FEATURE:
<223> OTHER INFORMATION: PRIMER

<400> SEQUENCE: 55
tcctatgagc tgacwcagcc a                                             21

<210> SEQ ID NO 56
<211> LENGTH: 22
<212> TYPE: DNA
<213> ORGANISM: Artificial Sequence
<220> FEATURE:
<223> OTHER INFORMATION: PRIMER

<400> SEQUENCE: 56
tcttctgagc tgactcagga cc                                            22

<210> SEQ ID NO 57
<211> LENGTH: 20
<212> TYPE: DNA
<213> ORGANISM: Artificial Sequence
<220> FEATURE:

<223> OTHER INFORMATION: PRIMER

<400> SEQUENCE: 57
cagsctgtgc tgactcagcc                                          20

<210> SEQ ID NO 58
<211> LENGTH: 22
<212> TYPE: DNA
<213> ORGANISM: Artificial Sequence
<220> FEATURE:
<223> OTHER INFORMATION: PRIMER

<400> SEQUENCE: 58
cagcctgtgc tgactcaatc at                                       22

<210> SEQ ID NO 59
<211> LENGTH: 21
<212> TYPE: DNA
<213> ORGANISM: Artificial Sequence
<220> FEATURE:
<223> OTHER INFORMATION: PRIMER

<400> SEQUENCE: 59
cagcttgtgc tgactcaatc g                                        21

<210> SEQ ID NO 60
<211> LENGTH: 24
<212> TYPE: DNA
<213> ORGANISM: Artificial Sequence
<220> FEATURE:
<223> OTHER INFORMATION: PRIMER

<400> SEQUENCE: 60
aattttatgc tgactcagcc ccac                                     24

<210> SEQ ID NO 61
<211> LENGTH: 22
<212> TYPE: DNA
<213> ORGANISM: Artificial Sequence
<220> FEATURE:
<223> OTHER INFORMATION: PRIMER

<400> SEQUENCE: 61
cagrctgtgg tgacycagga gc                                       22

<210> SEQ ID NO 62
<211> LENGTH: 20
<212> TYPE: DNA
<213> ORGANISM: Artificial Sequence
<220> FEATURE:
<223> OTHER INFORMATION: PRIMER

<400> SEQUENCE: 62
caggcagggc tgactcagcc                                          20

<210> SEQ ID NO 63
<211> LENGTH: 20
<212> TYPE: DNA
<213> ORGANISM: Artificial Sequence
<220> FEATURE:
<223> OTHER INFORMATION: PRIMER

<400> SEQUENCE: 63
aggtgtgcac gccgctggtc                                          20

```
<210> SEQ ID NO 64
<211> LENGTH: 23
<212> TYPE: DNA
<213> ORGANISM: Artificial Sequence
<220> FEATURE:
<223> OTHER INFORMATION: PRIMER

<400> SEQUENCE: 64
ggttcgggga agtagtcctt gac                                            23

<210> SEQ ID NO 65
<211> LENGTH: 24
<212> TYPE: DNA
<213> ORGANISM: Artificial Sequence
<220> FEATURE:
<223> OTHER INFORMATION: PRIMER

<400> SEQUENCE: 65
gtttctcgta gtctgctttg ctca                                           24

<210> SEQ ID NO 66
<211> LENGTH: 22
<212> TYPE: DNA
<213> ORGANISM: Artificial Sequence
<220> FEATURE:
<223> OTHER INFORMATION: PRIMER

<400> SEQUENCE: 66
gtgctgtcct tgctgtcctg ct                                             22

<210> SEQ ID NO 67
<211> LENGTH: 23
<212> TYPE: DNA
<213> ORGANISM: Artificial Sequence
<220> FEATURE:
<223> OTHER INFORMATION: PRIMER

<400> SEQUENCE: 67
ttggagggtk tggtggtctc cac                                            23

<210> SEQ ID NO 68
<211> LENGTH: 20
<212> TYPE: DNA
<213> ORGANISM: Artificial Sequence
<220> FEATURE:
<223> OTHER INFORMATION: PRIMER

<400> SEQUENCE: 68
ttgacggggc tgcyatctgc                                                20

<210> SEQ ID NO 69
<211> LENGTH: 21
<212> TYPE: DNA
<213> ORGANISM: Artificial Sequence
<220> FEATURE:
<223> OTHER INFORMATION: PRIMER

<400> SEQUENCE: 69
cacrgctccc gggtagaagt c                                              21

<210> SEQ ID NO 70
<211> LENGTH: 41
<212> TYPE: DNA
<213> ORGANISM: Artificial Sequence
<220> FEATURE:
<223> OTHER INFORMATION: PRIMER
```

<400> SEQUENCE: 70
gttgctacgc gtgtcctgag csaggtgcag ctggtgsagt c         41

<210> SEQ ID NO 71
<211> LENGTH: 41
<212> TYPE: DNA
<213> ORGANISM: Artificial Sequence
<220> FEATURE:
<223> OTHER INFORMATION: PRIMER

<400> SEQUENCE: 71
gttgctacgc gtgtcctgag ccaggtccag cttgtgcagt c         41

<210> SEQ ID NO 72
<211> LENGTH: 41
<212> TYPE: DNA
<213> ORGANISM: Artificial Sequence
<220> FEATURE:
<223> OTHER INFORMATION: PRIMER

<400> SEQUENCE: 72
gttgctacgc gtgtcctgag ccaggttcag ctggtgcagt c         41

<210> SEQ ID NO 73
<211> LENGTH: 43
<212> TYPE: DNA
<213> ORGANISM: Artificial Sequence
<220> FEATURE:
<223> OTHER INFORMATION: PRIMER

<400> SEQUENCE: 73
gttgctacgc gtgtcctgag ccaggtccag ctggtacagt ctg       43

<210> SEQ ID NO 74
<211> LENGTH: 43
<212> TYPE: DNA
<213> ORGANISM: Artificial Sequence
<220> FEATURE:
<223> OTHER INFORMATION: PRIMER

<400> SEQUENCE: 74
gttgctacgc gtgtcctgag ccaggtcacc ttgarggagt ctg       43

<210> SEQ ID NO 75
<211> LENGTH: 42
<212> TYPE: DNA
<213> ORGANISM: Artificial Sequence
<220> FEATURE:
<223> OTHER INFORMATION: PRIMER

<400> SEQUENCE: 75
gttgctacgc gtgtcctgag cgaggtgcag ctgttggagt ct        42

<210> SEQ ID NO 76
<211> LENGTH: 40
<212> TYPE: DNA
<213> ORGANISM: Artificial Sequence
<220> FEATURE:
<223> OTHER INFORMATION: PRIMER

<400> SEQUENCE: 76
gttgctacgc gtgtcctgag ccagstgcag ctgcaggagt          40

<210> SEQ ID NO 77
<211> LENGTH: 42

<212> TYPE: DNA
<213> ORGANISM: Artificial Sequence
<220> FEATURE:
<223> OTHER INFORMATION: PRIMER

<400> SEQUENCE: 77
gttgctacgc gtgtcctgag ccaggtgcag ctacarcagt gg          42

<210> SEQ ID NO 78
<211> LENGTH: 42
<212> TYPE: DNA
<213> ORGANISM: Artificial Sequence
<220> FEATURE:
<223> OTHER INFORMATION: PRIMER

<400> SEQUENCE: 78
gttgctacgc gtgtcctgag ccaggtacag ctgcagcagt ca          42

<210> SEQ ID NO 79
<211> LENGTH: 40
<212> TYPE: DNA
<213> ORGANISM: Artificial Sequence
<220> FEATURE:
<223> OTHER INFORMATION: PRIMER

<400> SEQUENCE: 79
gttgctacgc gtgtcctgag ccaggtgcag ctggtgcaat            40

<210> SEQ ID NO 80
<211> LENGTH: 39
<212> TYPE: DNA
<213> ORGANISM: Artificial Sequence
<220> FEATURE:
<223> OTHER INFORMATION: PRIMER

<400> SEQUENCE: 80
gatgggccct tggtgctagc tgaggagacg gtgaccagg             39

<210> SEQ ID NO 81
<211> LENGTH: 41
<212> TYPE: DNA
<213> ORGANISM: Artificial Sequence
<220> FEATURE:
<223> OTHER INFORMATION: PRIMER

<400> SEQUENCE: 81
gatgggccct tggtgctagc tgaggagaca gtgaccaggg t           41

<210> SEQ ID NO 82
<211> LENGTH: 42
<212> TYPE: DNA
<213> ORGANISM: Artificial Sequence
<220> FEATURE:
<223> OTHER INFORMATION: PRIMER

<400> SEQUENCE: 82
gatgggccct tggtgctagc tgaagagacg gtgaccattg tc          42

<210> SEQ ID NO 83
<211> LENGTH: 39
<212> TYPE: DNA
<213> ORGANISM: Artificial Sequence
<220> FEATURE:
<223> OTHER INFORMATION: PRIMER

<400> SEQUENCE: 83
gatgggccct tggtgctagc tgaggagacg gtgaccgtg    39

<210> SEQ ID NO 84
<211> LENGTH: 43
<212> TYPE: DNA
<213> ORGANISM: Artificial Sequence
<220> FEATURE:
<223> OTHER INFORMATION: PRIMER

<400> SEQUENCE: 84
ggctcccagg tgcacgatgt gacatccagw tgacccagtc tcc    43

<210> SEQ ID NO 85
<211> LENGTH: 48
<212> TYPE: DNA
<213> ORGANISM: Artificial Sequence
<220> FEATURE:
<223> OTHER INFORMATION: PRIMER

<400> SEQUENCE: 85
ggctcccagg tgcacgatgt gatattgtga tgacccagac tccactct    48

<210> SEQ ID NO 86
<211> LENGTH: 45
<212> TYPE: DNA
<213> ORGANISM: Artificial Sequence
<220> FEATURE:
<223> OTHER INFORMATION: PRIMER

<400> SEQUENCE: 86
ggctcccagg tgcacgatgt gaaattgtgt tgacrcagtc tccag    45

<210> SEQ ID NO 87
<211> LENGTH: 42
<212> TYPE: DNA
<213> ORGANISM: Artificial Sequence
<220> FEATURE:
<223> OTHER INFORMATION: PRIMER

<400> SEQUENCE: 87
ggctcccagg tgcacgatgt gacatcgtga tgacccagtc tc    42

<210> SEQ ID NO 88
<211> LENGTH: 42
<212> TYPE: DNA
<213> ORGANISM: Artificial Sequence
<220> FEATURE:
<223> OTHER INFORMATION: PRIMER

<400> SEQUENCE: 88
ggctcccagg tgcacgatgt gaaacgacac tcacgcagtc tc    42

<210> SEQ ID NO 89
<211> LENGTH: 44
<212> TYPE: DNA
<213> ORGANISM: Artificial Sequence
<220> FEATURE:
<223> OTHER INFORMATION: PRIMER

<400> SEQUENCE: 89
ggctcccagg tgcacgatgt gaaattgtgc tgactcagtc tcca    44

<210> SEQ ID NO 90
<211> LENGTH: 37
<212> TYPE: DNA
<213> ORGANISM: Artificial Sequence

<220> FEATURE:
<223> OTHER INFORMATION: PRIMER

<400> SEQUENCE: 90
tgcagccacc gtacgtttga tttccacctt ggtccct                    37

<210> SEQ ID NO 91
<211> LENGTH: 37
<212> TYPE: DNA
<213> ORGANISM: Artificial Sequence
<220> FEATURE:
<223> OTHER INFORMATION: PRIMER

<400> SEQUENCE: 91
tgcagccacc gtacgtttga tctccagctt ggtccct                    37

<210> SEQ ID NO 92
<211> LENGTH: 37
<212> TYPE: DNA
<213> ORGANISM: Artificial Sequence
<220> FEATURE:
<223> OTHER INFORMATION: PRIMER

<400> SEQUENCE: 92
tgcagccacc gtacgtttga tatccacttt ggtccca                    37

<210> SEQ ID NO 93
<211> LENGTH: 37
<212> TYPE: DNA
<213> ORGANISM: Artificial Sequence
<220> FEATURE:
<223> OTHER INFORMATION: PRIMER

<400> SEQUENCE: 93
tgcagccacc gtacgtttga tctccacctt ggtccct                    37

<210> SEQ ID NO 94
<211> LENGTH: 38
<212> TYPE: DNA
<213> ORGANISM: Artificial Sequence
<220> FEATURE:
<223> OTHER INFORMATION: PRIMER

<400> SEQUENCE: 94
tgcagccacc gtacgtttaa tctccagtcg tgtccctt                   38

<210> SEQ ID NO 95
<211> LENGTH: 49
<212> TYPE: DNA
<213> ORGANISM: Artificial Sequence
<220> FEATURE:
<223> OTHER INFORMATION: PRIMER

<400> SEQUENCE: 95
tccttgctta tgggtccgga gtggattctc agtctgtgyt gacgcagcc       49

<210> SEQ ID NO 96
<211> LENGTH: 50
<212> TYPE: DNA
<213> ORGANISM: Artificial Sequence
<220> FEATURE:
<223> OTHER INFORMATION: PRIMER

<400> SEQUENCE: 96
tccttgctta tgggtccgga gtggattctc agtctgtgct gactcagcca      50

<210> SEQ ID NO 97
<211> LENGTH: 49
<212> TYPE: DNA
<213> ORGANISM: Artificial Sequence
<220> FEATURE:
<223> OTHER INFORMATION: PRIMER

<400> SEQUENCE: 97
tccttgctta tgggtccgga gtggattctc agtctgccct gactcagcc          49

<210> SEQ ID NO 98
<211> LENGTH: 50
<212> TYPE: DNA
<213> ORGANISM: Artificial Sequence
<220> FEATURE:
<223> OTHER INFORMATION: PRIMER

<400> SEQUENCE: 98
tccttgctta tgggtccgga gtggattctt cctatgagct gacwcagcca          50

<210> SEQ ID NO 99
<211> LENGTH: 50
<212> TYPE: DNA
<213> ORGANISM: Artificial Sequence
<220> FEATURE:
<223> OTHER INFORMATION: PRIMER

<400> SEQUENCE: 99
tccttgctta tgggtccgga gtggattctt cttctgagct gactcaggac          50

<210> SEQ ID NO 100
<211> LENGTH: 49
<212> TYPE: DNA
<213> ORGANISM: Artificial Sequence
<220> FEATURE:
<223> OTHER INFORMATION: PRIMER

<400> SEQUENCE: 100
tccttgctta tgggtccgga gtggattctc agsctgtgct gactcagcc          49

<210> SEQ ID NO 101
<211> LENGTH: 49
<212> TYPE: DNA
<213> ORGANISM: Artificial Sequence
<220> FEATURE:
<223> OTHER INFORMATION: PRIMER

<400> SEQUENCE: 101
tccttgctta tgggtccgga gtggattctc agyctgtgct gactcaatc          49

<210> SEQ ID NO 102
<211> LENGTH: 50
<212> TYPE: DNA
<213> ORGANISM: Artificial Sequence
<220> FEATURE:
<223> OTHER INFORMATION: PRIMER

<400> SEQUENCE: 102
tccttgctta tgggtccgga gtggattcta attttatgct gactcagccc          50

<210> SEQ ID NO 103
<211> LENGTH: 50
<212> TYPE: DNA
<213> ORGANISM: Artificial Sequence
<220> FEATURE:
<223> OTHER INFORMATION: PRIMER -continued

<400> SEQUENCE: 103
tccttgctta tgggtccgga gtggattctc agrctgtggt gacycaggag                50

<210> SEQ ID NO 104
<211> LENGTH: 49
<212> TYPE: DNA
<213> ORGANISM: Artificial Sequence
<220> FEATURE:
<223> OTHER INFORMATION: PRIMER

<400> SEQUENCE: 104
tccttgctta tgggtccgga gtggattctc aggcagggct gactcagcc                 49

<210> SEQ ID NO 105
<211> LENGTH: 35
<212> TYPE: DNA
<213> ORGANISM: Artificial Sequence
<220> FEATURE:
<223> OTHER INFORMATION: PRIMER

<400> SEQUENCE: 105
ggccttgggc tgacctagga cggtgacctt ggtcc                                35

<210> SEQ ID NO 106
<211> LENGTH: 35
<212> TYPE: DNA
<213> ORGANISM: Artificial Sequence
<220> FEATURE:
<223> OTHER INFORMATION: PRIMER

<400> SEQUENCE: 106
ggccttgggc tgacctagga cggtcagctt ggtcc                                35

<210> SEQ ID NO 107
<211> LENGTH: 35
<212> TYPE: DNA
<213> ORGANISM: Artificial Sequence
<220> FEATURE:
<223> OTHER INFORMATION: PRIMER

<400> SEQUENCE: 107
ggccttgggc tgacctagga cggtcacctt ggtgc                                35

<210> SEQ ID NO 108
<211> LENGTH: 35
<212> TYPE: DNA
<213> ORGANISM: Artificial Sequence
<220> FEATURE:
<223> OTHER INFORMATION: PRIMER

<400> SEQUENCE: 108
ggccttgggc tgacctagga cggtcagctg ggtgc                                35

<210> SEQ ID NO 109
<211> LENGTH: 124
<212> TYPE: PRT
<213> ORGANISM: Homo sapiens

<400> SEQUENCE: 109

Glu Val Gln Leu Val Glu Ser Gly Gly Gly Leu Val Lys Pro Gly Asp
1               5                   10                  15

Ser Leu Thr Val Ser Cys Val Ala Ser Gly Phe Thr Phe Ser Asn Tyr
            20                  25                  30

Phe Ile His Trp Val Arg Gln Ala Pro Gly Lys Gly Leu Glu Trp Val
        35                  40                  45

Ala Thr Ile Ser Gly Arg Thr Lys Tyr Met Phe Tyr Ser Asp Ser Leu
 50                  55                  60

Arg Gly Arg Phe Thr Val Ser Arg Asp Asn Ala Asn Asn Ser Val Tyr
 65                  70                  75                  80

Leu His Met Ser Ser Leu Arg Gly Glu Asp Thr Ala Leu Tyr Tyr Cys
                 85                  90                  95

Val Arg Gly Tyr Asp His Ser Asp Ser Asn Ser Ala Ala Asp Leu Leu
                100                 105                 110

His Trp Gly Arg Gly Thr Leu Val Thr Val Ser Ser
        115                 120

<210> SEQ ID NO 110
<211> LENGTH: 124
<212> TYPE: PRT
<213> ORGANISM: Homo sapiens

<400> SEQUENCE: 110

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Pro Phe Ser Arg Tyr
                20                  25                  30

Ser Met His Trp Val Arg Gln Ala Pro Gly Lys Gly Leu Glu Trp Val
        35                  40                  45

Ser Ser Met Thr Ser Arg Thr Asn His Lys Tyr Tyr Ala Asp Ser Leu
 50                  55                  60

Lys Gly Arg Phe Leu Ile Ser Arg Asp Asn Asp Arg Asp Ser Leu Tyr
 65                  70                  75                  80

Leu Glu Met Asn Ser Leu Gly Val Glu Asp Thr Ala Ile Tyr Phe Cys
                 85                  90                  95

Ala Arg Gly Tyr Asp Thr Ser Gly Ser Asp Ser Gly Val Asp Phe Gln
                100                 105                 110

Tyr Trp Gly Gln Gly Thr Leu Val Thr Val Ser Ser
        115                 120

<210> SEQ ID NO 111
<211> LENGTH: 121
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly
 1               5                  10                  15

Pro Leu Arg Leu Ser Cys Ala Ala Ser Gly Phe Thr Phe Ser Ile Tyr
                20                  25                  30

Ser Met Asn Trp Val Arg Gln Ala Pro Gly Lys Gly Leu Glu Trp Val
        35                  40                  45

Ser Ser Ile Ser Gly Ser Gly Asp Asn Thr Tyr Tyr Ala Asp Ser Val
 50                  55                  60

Lys Gly Arg Phe Thr Ile Thr Arg Asp Ser Ser Lys Asn Thr Leu Tyr
 65                  70                  75                  80

Leu Gln Met Asn Thr Leu Arg Ala Glu Asp Thr Ala Val Tyr Phe Cys
                 85                  90                  95

Ala Lys Ser Gly Arg Asn Ile Ile Ser Pro Gly Phe Asp Ser Trp Gly
                100                 105                 110

```
Gln Gly Thr Leu Val Thr Val Ser Ser
        115                 120
```

<210> SEQ ID NO 112
<211> LENGTH: 122
<212> TYPE: PRT
<213> ORGANISM: Homo sapiens

<400> SEQUENCE: 112

```
Glu Val Gln Leu Val Glu Ser Gly Gly Gly Leu Val Lys Pro Gly Glu
1               5                   10                  15

Ser Leu Arg Leu Ala Cys Val Ala Ser Gly Phe Asn Phe Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Asn Ser Gly Ser His Thr Tyr Tyr Ala Asp Ala Val
    50                  55                  60

Lys Gly Arg Phe Thr Val Ser Arg Asp Asn Ala Lys Asn Ser Leu Tyr
65                  70                  75                  80

Leu Gln Met Thr Ser Leu Arg Gly Glu Asp Thr Ala Ile Tyr Phe Cys
                85                  90                  95

Ala Arg Asp Pro Ser Ile Met Arg Gly Thr Tyr Tyr Met Asp Val Trp
            100                 105                 110

Gly Lys Gly Thr Thr Val Thr Val Ser Ser
        115                 120
```

<210> SEQ ID NO 113
<211> LENGTH: 111
<212> TYPE: PRT
<213> ORGANISM: Homo sapiens

<400> SEQUENCE: 113

```
Asn Phe Met Leu Thr Gln Pro Leu Ser Val Ser Gly Tyr Pro Gly Lys
1               5                   10                  15

Thr Ile Val Ile Ser Cys Val Arg Ser Ser Gly Ser Val Ala Ser His
            20                  25                  30

Tyr Val Gln Trp Phe Gln Arg Pro Gly Ser Ala Pro Ala Met Val
        35                  40                  45

Ile Tyr Glu Asp Ser His Arg Pro Ser Gly Ile Pro Asp Arg Phe Ser
    50                  55                  60

Gly Ser Val Asp Ala Ser Ser Asn Ser Ala Ser Leu Thr Ile Ser Gly
65                  70                  75                  80

Leu Lys Thr Glu Asp Glu Ala Asp Tyr Phe Cys Gln Ser Tyr Tyr Gly
                85                  90                  95

Asn Asn Gln Val Leu Phe Gly Gly Thr Lys Leu Thr Val Leu
            100                 105                 110
```

<210> SEQ ID NO 114
<211> LENGTH: 111
<212> TYPE: PRT
<213> ORGANISM: Homo sapiens

<400> SEQUENCE: 114

```
Asn Phe Met Leu Thr Gln Pro His Ser Val Ser Glu Ser Pro Gly Lys
1               5                   10                  15

Thr Ile Thr Ile Ser Cys Thr Arg Gly Arg Gly Tyr Ile Ala Ser Tyr
            20                  25                  30

Tyr Val Gln Trp Tyr Gln Gln Arg Pro Gly Gly Val Pro Lys Ile Val
```

```
                35                  40                  45
Val Phe Glu Asp Thr Gln Arg Pro Ser Gly Val Pro Asp Arg Ile Ser
 50                  55                  60
Gly Ser Ile Asp Thr Ser Thr Asn Ser Ala Ser Leu Thr Ile Ser Gly
 65                  70                  75                  80
Leu Gln Thr Glu Asp Glu Ala Asp Tyr Tyr Cys Gln Ser Tyr Asp Asp
                 85                  90                  95
Ala Asn His Val Ile Phe Gly Gly Gly Thr Lys Leu Thr Val Leu
                100                 105                 110
```

<210> SEQ ID NO 115
<211> LENGTH: 116
<212> TYPE: PRT
<213> ORGANISM: Homo sapiens

<400> SEQUENCE: 115

```
Gln Pro Val Leu Thr Gln Pro Ser Ala Ser Ala Ser Leu Gly Ala
 1               5                  10                  15
Ser Val Thr Leu Thr Cys Thr Leu Asn Ser Asp Tyr Gly Asp Tyr Lys
                 20                  25                  30
Val Asp Trp Tyr Gln Gln Arg Pro Gly Lys Gly Pro Arg Phe Val Met
                 35                  40                  45
Arg Val Gly Thr Gly Gly Ile Val Gly Ser Lys Gly Asp Gly Ile Pro
 50                  55                  60
Asp Arg Phe Ser Val Leu Gly Ser Gly Leu Asn Arg Phe Leu Thr Ile
 65                  70                  75                  80
Lys Asn Ile Gln Glu Glu Asp Glu Ser Asp Tyr Tyr Cys Gly Ala Asp
                 85                  90                  95
His Gly Ser Ala Asn Asn Phe Ile Trp Val Phe Gly Gly Gly Thr Lys
                100                 105                 110
Leu Thr Val Leu
        115
```

<210> SEQ ID NO 116
<211> LENGTH: 110
<212> TYPE: PRT
<213> ORGANISM: Homo sapiens

<400> SEQUENCE: 116

```
Gln Ser Val Leu Thr Gln Pro Pro Ser Ala Ser Gly Thr Pro Gly Gln
 1               5                  10                  15
Arg Val Thr Ile Ser Cys Ser Gly Ser Ser Ser Asn Ile Gly Thr Asn
                 20                  25                  30
Pro Val Ser Trp Tyr Gln Gln Phe Pro Gly Met Ala Pro Lys Leu Leu
                 35                  40                  45
Ile Tyr Phe Asn Asn Gln Arg Pro Ser Gly Val Pro Glu Arg Phe Ser
 50                  55                  60
Gly Ser Lys Ser Gly Thr Pro Ala Ser Leu Ala Ile Gly Gly Leu Gln
 65                  70                  75                  80
Ser Glu Asp Glu Ala Asn Tyr Tyr Cys Ala Ser Trp Asp Asp Thr Leu
                 85                  90                  95
Asn Gly Leu Val Phe Gly Gly Gly Thr Lys Leu Thr Val Leu
                100                 105                 110
```

<210> SEQ ID NO 117
<211> LENGTH: 20
<212> TYPE: DNA

```
<213> ORGANISM: Artificial Sequence
<220> FEATURE:
<223> OTHER INFORMATION: PRIMER

<400> SEQUENCE: 117
gctcccaggt gcacgatgtg                                               20

<210> SEQ ID NO 118
<211> LENGTH: 24
<212> TYPE: DNA
<213> ORGANISM: Artificial Sequence
<220> FEATURE:
<223> OTHER INFORMATION: PRIMER

<400> SEQUENCE: 118
gcttatgggt ccggagtgga ttct                                          24

<210> SEQ ID NO 119
<211> LENGTH: 20
<212> TYPE: DNA
<213> ORGANISM: Artificial Sequence
<220> FEATURE:
<223> OTHER INFORMATION: PRIMER

<400> SEQUENCE: 119
gatgggccct tggtgctagc                                               20

<210> SEQ ID NO 120
<211> LENGTH: 8
<212> TYPE: PRT
<213> ORGANISM: Homo sapiens

<400> SEQUENCE: 120

Gly Phe Thr Phe Ser Asn Tyr Phe
1               5

<210> SEQ ID NO 121
<211> LENGTH: 8
<212> TYPE: PRT
<213> ORGANISM: Homo sapiens

<400> SEQUENCE: 121

Ile Ser Gly Arg Thr Lys Tyr Met
1               5

<210> SEQ ID NO 122
<211> LENGTH: 17
<212> TYPE: PRT
<213> ORGANISM: Homo sapiens

<400> SEQUENCE: 122

Val Arg Gly Tyr Asp His Ser Asp Ser Asn Ser Ala Ala Asp Leu Leu
1               5                   10                  15

His

<210> SEQ ID NO 123
<211> LENGTH: 8
<212> TYPE: PRT
<213> ORGANISM: Homo sapiens

<400> SEQUENCE: 123

Gly Phe Pro Phe Ser Arg Tyr Ser
1               5
```

```
<210> SEQ ID NO 124
<211> LENGTH: 8
<212> TYPE: PRT
<213> ORGANISM: Homo sapiens

<400> SEQUENCE: 124

Met Thr Ser Arg Thr Asn His Lys
1               5

<210> SEQ ID NO 125
<211> LENGTH: 17
<212> TYPE: PRT
<213> ORGANISM: Homo sapiens

<400> SEQUENCE: 125

Ala Arg Gly Tyr Asp Thr Ser Gly Ser Asp Ser Gly Val Asp Phe Gln
1               5                   10                  15

Tyr

<210> SEQ ID NO 126
<211> LENGTH: 8
<212> TYPE: PRT
<213> ORGANISM: Homo sapiens

<400> SEQUENCE: 126

Gly Phe Thr Phe Ser Ile Tyr Ser
1               5

<210> SEQ ID NO 127
<211> LENGTH: 8
<212> TYPE: PRT
<213> ORGANISM: Homo sapiens

<400> SEQUENCE: 127

Ile Ser Gly Ser Gly Asp Asn Thr
1               5

<210> SEQ ID NO 128
<211> LENGTH: 14
<212> TYPE: PRT
<213> ORGANISM: Homo sapiens

<400> SEQUENCE: 128

Ala Lys Ser Gly Arg Asn Ile Ile Ser Pro Gly Phe Asp Ser
1               5                   10

<210> SEQ ID NO 129
<211> LENGTH: 8
<212> TYPE: PRT
<213> ORGANISM: Homo sapiens

<400> SEQUENCE: 129

Gly Phe Asn Phe Ser Asp Tyr Tyr
1               5

<210> SEQ ID NO 130
<211> LENGTH: 8
<212> TYPE: PRT
<213> ORGANISM: Homo sapiens

<400> SEQUENCE: 130

Ile Ser Asn Ser Gly Ser His Thr
1               5
```

```
<210> SEQ ID NO 131
<211> LENGTH: 15
<212> TYPE: PRT
<213> ORGANISM: Homo sapiens

<400> SEQUENCE: 131

Ala Arg Asp Pro Ser Ile Met Arg Gly Thr Tyr Tyr Met Asp Val
1               5                   10                  15

<210> SEQ ID NO 132
<211> LENGTH: 8
<212> TYPE: PRT
<213> ORGANISM: Homo sapiens

<400> SEQUENCE: 132

Ser Gly Ser Val Ala Ser His Tyr
1               5

<210> SEQ ID NO 133
<211> LENGTH: 3
<212> TYPE: PRT
<213> ORGANISM: Homo sapiens

<400> SEQUENCE: 133

Glu Asp Ser
1

<210> SEQ ID NO 134
<211> LENGTH: 10
<212> TYPE: PRT
<213> ORGANISM: Homo sapiens

<400> SEQUENCE: 134

Gln Ser Tyr Tyr Gly Asn Asn Gln Val Leu
1               5                   10

<210> SEQ ID NO 135
<211> LENGTH: 8
<212> TYPE: PRT
<213> ORGANISM: Homo sapiens

<400> SEQUENCE: 135

Arg Gly Tyr Ile Ala Ser Tyr Tyr
1               5

<210> SEQ ID NO 136
<211> LENGTH: 3
<212> TYPE: PRT
<213> ORGANISM: Homo sapiens

<400> SEQUENCE: 136

Glu Asp Thr
1

<210> SEQ ID NO 137
<211> LENGTH: 10
<212> TYPE: PRT
<213> ORGANISM: Homo sapiens

<400> SEQUENCE: 137

Gln Ser Tyr Asp Asp Ala Asn His Val Ile
1               5                   10

<210> SEQ ID NO 138
<211> LENGTH: 7
```

<212> TYPE: PRT
<213> ORGANISM: Homo sapiens

<400> SEQUENCE: 138

Ser Asp Tyr Gly Asp Tyr Lys
1               5

<210> SEQ ID NO 139
<211> LENGTH: 8
<212> TYPE: PRT
<213> ORGANISM: Homo sapiens

<400> SEQUENCE: 139

Val Gly Thr Gly Gly Ile Val Gly
1               5

<210> SEQ ID NO 140
<211> LENGTH: 13
<212> TYPE: PRT
<213> ORGANISM: Homo sapiens

<400> SEQUENCE: 140

Gly Ala Asp His Gly Ser Ala Asn Asn Phe Ile Trp Val
1               5                   10

<210> SEQ ID NO 141
<211> LENGTH: 8
<212> TYPE: PRT
<213> ORGANISM: Homo sapiens

<400> SEQUENCE: 141

Ser Ser Asn Ile Gly Thr Asn Pro
1               5

<210> SEQ ID NO 142
<211> LENGTH: 3
<212> TYPE: PRT
<213> ORGANISM: Homo sapiens

<400> SEQUENCE: 142

Phe Asn Asn
1

<210> SEQ ID NO 143
<211> LENGTH: 11
<212> TYPE: PRT
<213> ORGANISM: Homo sapiens

<400> SEQUENCE: 143

Ala Ser Trp Asp Asp Thr Leu Asn Gly Leu Val
1               5                   10

<210> SEQ ID NO 144
<211> LENGTH: 10
<212> TYPE: PRT
<213> ORGANISM: Homo sapiens

<400> SEQUENCE: 144

Gly Phe Thr Phe Ser Asn Tyr Phe Ile His
1               5                   10

<210> SEQ ID NO 145
<211> LENGTH: 17
<212> TYPE: PRT
<213> ORGANISM: Homo sapiens

```
<400> SEQUENCE: 145

Thr Ile Ser Gly Arg Thr Lys Tyr Met Phe Tyr Ser Asp Ser Leu Arg
1               5                   10                  15

Gly

<210> SEQ ID NO 146
<211> LENGTH: 15
<212> TYPE: PRT
<213> ORGANISM: Homo sapiens

<400> SEQUENCE: 146

Gly Tyr Asp His Ser Asp Ser Asn Ser Ala Ala Asp Leu Leu His
1               5                   10                  15

<210> SEQ ID NO 147
<211> LENGTH: 10
<212> TYPE: PRT
<213> ORGANISM: Homo sapiens

<400> SEQUENCE: 147

Gly Phe Pro Phe Ser Arg Tyr Ser Met His
1               5                   10

<210> SEQ ID NO 148
<211> LENGTH: 17
<212> TYPE: PRT
<213> ORGANISM: Homo sapiens

<400> SEQUENCE: 148

Ser Met Thr Ser Arg Thr Asn His Lys Tyr Tyr Ala Asp Ser Leu Lys
1               5                   10                  15

Gly

<210> SEQ ID NO 149
<211> LENGTH: 15
<212> TYPE: PRT
<213> ORGANISM: Homo sapiens

<400> SEQUENCE: 149

Gly Tyr Asp Thr Ser Gly Ser Asp Ser Gly Val Asp Phe Gln Tyr
1               5                   10                  15

<210> SEQ ID NO 150
<211> LENGTH: 10
<212> TYPE: PRT
<213> ORGANISM: Homo sapiens

<400> SEQUENCE: 150

Gly Phe Thr Phe Ser Ile Tyr Ser Met Asn
1               5                   10

<210> SEQ ID NO 151
<211> LENGTH: 17
<212> TYPE: PRT
<213> ORGANISM: Homo sapiens

<400> SEQUENCE: 151

Ser Ile Ser Gly Ser Gly Asp Asn Thr Tyr Tyr Ala Asp Ser Val Lys
1               5                   10                  15

Gly
```

```
<210> SEQ ID NO 152
<211> LENGTH: 11
<212> TYPE: PRT
<213> ORGANISM: Homo sapiens

<400> SEQUENCE: 152

Ser Gly Arg Asn Ile Ser Pro Gly Phe Asp Ser
1               5                   10

<210> SEQ ID NO 153
<211> LENGTH: 10
<212> TYPE: PRT
<213> ORGANISM: Homo sapiens

<400> SEQUENCE: 153

Gly Phe Asn Phe Ser Asp Tyr Tyr Met Thr
1               5                   10

<210> SEQ ID NO 154
<211> LENGTH: 17
<212> TYPE: PRT
<213> ORGANISM: Homo sapiens

<400> SEQUENCE: 154

Tyr Ile Ser Asn Ser Gly Ser His Thr Tyr Tyr Ala Asp Ala Val Lys
1               5                   10                  15

Gly

<210> SEQ ID NO 155
<211> LENGTH: 13
<212> TYPE: PRT
<213> ORGANISM: Homo sapiens

<400> SEQUENCE: 155

Asp Pro Ser Ile Met Arg Gly Thr Tyr Tyr Met Asp Val
1               5                   10

<210> SEQ ID NO 156
<211> LENGTH: 13
<212> TYPE: PRT
<213> ORGANISM: Homo sapiens

<400> SEQUENCE: 156

Val Arg Ser Ser Gly Ser Val Ala Ser His Tyr Val Gln
1               5                   10

<210> SEQ ID NO 157
<211> LENGTH: 7
<212> TYPE: PRT
<213> ORGANISM: Homo sapiens

<400> SEQUENCE: 157

Glu Asp Ser His Arg Pro Ser
1               5

<210> SEQ ID NO 158
<211> LENGTH: 13
<212> TYPE: PRT
<213> ORGANISM: Homo sapiens

<400> SEQUENCE: 158

Thr Arg Gly Arg Gly Tyr Ile Ala Ser Tyr Tyr Val Gln
1               5                   10
```

-continued

<210> SEQ ID NO 159
<211> LENGTH: 7
<212> TYPE: PRT
<213> ORGANISM: Homo sapiens

<400> SEQUENCE: 159

Glu Asp Thr Gln Arg Pro Ser
1               5

<210> SEQ ID NO 160
<211> LENGTH: 12
<212> TYPE: PRT
<213> ORGANISM: Homo sapiens

<400> SEQUENCE: 160

Thr Leu Asn Ser Asp Tyr Gly Asp Tyr Lys Val Asp
1               5                   10

<210> SEQ ID NO 161
<211> LENGTH: 7
<212> TYPE: PRT
<213> ORGANISM: Homo sapiens

<400> SEQUENCE: 161

Val Gly Thr Gly Gly Ile Val
1               5

<210> SEQ ID NO 162
<211> LENGTH: 13
<212> TYPE: PRT
<213> ORGANISM: Homo sapiens

<400> SEQUENCE: 162

Ser Gly Ser Ser Ser Asn Ile Gly Thr Asn Pro Val Ser
1               5                   10

<210> SEQ ID NO 163
<211> LENGTH: 7
<212> TYPE: PRT
<213> ORGANISM: Homo sapiens

<400> SEQUENCE: 163

Phe Asn Asn Gln Arg Pro Ser
1               5

<210> SEQ ID NO 164
<211> LENGTH: 124
<212> TYPE: PRT
<213> ORGANISM: Artificial Sequence
<220> FEATURE:
<223> OTHER INFORMATION: ANTIBODY

<400> SEQUENCE: 164

Glu Val Gln Leu Val Glu Ser Gly Gly Leu Val Lys Pro Gly Asp
1               5                   10                  15

Ser Leu Thr Val Ser Cys Val Ala Ser Gly Phe Thr Phe Ser Asn Tyr
                20                  25                  30

Phe Ile His Trp Val Arg Gln Ala Pro Gly Lys Gly Leu Glu Trp Val
            35                  40                  45

Ala Thr Ile Ser Gly Arg Thr Lys Tyr Met Phe Tyr Ser Asp Ser Leu
        50                  55                  60

Arg Gly Arg Phe Thr Val Ser Arg Asp Asn Ala Ala Asn Ser Val Tyr
65                  70                  75                  80

Leu His Met Ser Ser Leu Arg Gly Glu Asp Thr Ala Leu Tyr Tyr Cys
                    85                  90                  95

Val Arg Gly Tyr Asp His Ser Asp Ser Asn Ser Ala Ala Asp Leu Leu
                100                 105                 110

His Trp Gly Arg Gly Thr Leu Val Thr Val Ser Ser
            115                 120

<210> SEQ ID NO 165
<211> LENGTH: 124
<212> TYPE: PRT
<213> ORGANISM: Artificial Sequence
<220> FEATURE:
<223> OTHER INFORMATION: ANTIBODY

<400> SEQUENCE: 165

Glu Val Gln Leu Val Glu Ser Gly Gly Leu Val Lys Pro Gly Asp
1               5                   10                  15

Ser Leu Thr Val Ser Cys Val Ala Ser Gly Phe Thr Phe Ser Asn Tyr
                20                  25                  30

Phe Ile His Trp Val Arg Gln Ala Pro Gly Lys Gly Leu Glu Trp Val
            35                  40                  45

Ala Thr Ile Ser Gly Arg Thr Lys Tyr Met Phe Tyr Ser Asp Ser Leu
50                  55                  60

Arg Gly Arg Phe Thr Val Ser Arg Asp Asn Ala Gln Asn Ser Val Tyr
65                  70                  75                  80

Leu His Met Ser Ser Leu Arg Gly Glu Asp Thr Ala Leu Tyr Tyr Cys
                85                  90                  95

Val Arg Gly Tyr Asp His Ser Asp Ser Asn Ser Ala Ala Asp Leu Leu
                100                 105                 110

His Trp Gly Arg Gly Thr Leu Val Thr Val Ser Ser
            115                 120

<210> SEQ ID NO 166
<211> LENGTH: 143
<212> TYPE: PRT
<213> ORGANISM: Homo sapiens

<400> SEQUENCE: 166

Gln Asp Pro Tyr Val Lys Glu Ala Glu Asn Leu Lys Lys Tyr Phe Asn
1               5                   10                  15

Ala Gly His Ser Asp Val Ala Asp Asn Gly Thr Leu Phe Leu Gly Ile
                20                  25                  30

Leu Lys Asn Trp Lys Glu Glu Ser Asp Arg Lys Ile Met Gln Ser Gln
            35                  40                  45

Ile Val Ser Phe Tyr Phe Lys Leu Phe Lys Asn Phe Lys Asp Asp Gln
50                  55                  60

Ser Ile Gln Lys Ser Val Glu Thr Ile Lys Glu Asp Met Asn Val Lys
65                  70                  75                  80

Phe Phe Asn Ser Asn Lys Lys Lys Arg Asp Asp Phe Glu Lys Leu Thr
                85                  90                  95

Asn Tyr Ser Val Thr Asp Leu Asn Val Gln Arg Lys Ala Ile His Glu
                100                 105                 110

Leu Ile Gln Val Met Ala Glu Leu Ser Pro Ala Ala Lys Thr Gly Lys
            115                 120                 125

Arg Lys Arg Ser Gln Met Leu Phe Arg Gly Arg Arg Ala Ser Gln
130                 135                 140

<210> SEQ ID NO 167
<211> LENGTH: 23
<212> TYPE: PRT
<213> ORGANISM: Homo sapiens

<400> SEQUENCE: 167

Leu Gly Ile Leu Lys Asn Trp Lys Glu Glu Ser Asp Arg Lys Ile Met
1               5                   10                  15

Gln Ser Gln Ile Val Ser Phe
            20

<210> SEQ ID NO 168
<211> LENGTH: 15
<212> TYPE: PRT
<213> ORGANISM: Homo sapiens

<400> SEQUENCE: 168

Asn Val Lys Phe Phe Asn Ser Asn Lys Lys Arg Asp Asp Phe
1               5                   10                  15

<210> SEQ ID NO 169
<211> LENGTH: 41
<212> TYPE: DNA
<213> ORGANISM: Artificial Sequence
<220> FEATURE:
<223> OTHER INFORMATION: PRIMER

<400> SEQUENCE: 169
cgtttctaga gacaacgccc agaattcggt atatctccac a                    41

<210> SEQ ID NO 170
<211> LENGTH: 40
<212> TYPE: DNA
<213> ORGANISM: Artificial Sequence
<220> FEATURE:
<223> OTHER INFORMATION: PRIMER

<400> SEQUENCE: 170
cgtttctaga gacaacgccg ccaattcggt atatctccac                      40

<210> SEQ ID NO 171
<211> LENGTH: 13
<212> TYPE: PRT
<213> ORGANISM: Homo sapiens

<400> SEQUENCE: 171

Trp Lys Glu Glu Ser Asp Arg Lys Ile Met Gln Ser Gln
1               5                   10

<210> SEQ ID NO 172
<211> LENGTH: 11
<212> TYPE: PRT
<213> ORGANISM: Homo sapiens

<400> SEQUENCE: 172

Phe Asn Ser Asn Lys Lys Lys Arg Asp Asp Phe
1               5                   10

<210> SEQ ID NO 173
<211> LENGTH: 373
<212> TYPE: DNA
<213> ORGANISM: Homo sapiens

<400> SEQUENCE: 173
gaggtgcagc tggtggagtc tgggggaggc ctggtcaagc cggggggactc tctgacagtc    60 tcctgtgtcg cctctggatt cactttcagc aactatttca tccactgggt ccgacaggct    120
ccagggaagg gactggagtg ggtcgcaacg atcagtggcc gtacgaaata tatgttctac    180
tcagactcat tgaggggccg attcaccgtt tctagagaca cgccaacaa ttcggtatat    240 ctccacatga gcagcctgag aggcgaagac acggctctct attactgtgt gagaggctat    300
gatcatagtg attccaactc ggcagcagac ctcctgcatt ggggccgggg caccctggtc    360
accgtctcct cag    373

<210> SEQ ID NO 174
<211> LENGTH: 334
<212> TYPE: DNA
<213> ORGANISM: Homo sapiens

<400> SEQUENCE: 174
aattttatgc tgactcagcc cctctctgtg tcgggctatc cgggaaagac gatagtcatc    60
tcctgtgtcc ggagcagtgg cagcgtggcc agccactatg tgcagtggtt ccaacagcgc    120
ccgggcagtg cccccgccat ggtgatttat gaagatagcc acagaccttc tgggattcct    180
gatcgattct ctggctccgt cgacgcctcc tccaactctg cctccctcac catctctgga    240
ctgaagactg aggacgaggc tgactacttc tgtcaatctt attatggcaa caatcaggtt    300
ctcttcggcg gcgggaccaa gctgaccgtc ctag    334

<210> SEQ ID NO 175
<211> LENGTH: 373
<212> TYPE: DNA
<213> ORGANISM: Artificial Sequence
<220> FEATURE:
<223> OTHER INFORMATION: ANTIBODY

<400> SEQUENCE: 175
gaggtgcagc tggtggagtc tgggggaggc ctggtcaagc cggggggactc tctgacagtc    60 tcctgtgtcg cctctggatt cactttcagc aactatttca tccactgggt ccgacaggct    120
ccagggaagg gactggagtg ggtcgcaacg atcagtggcc gtacgaaata tatgttctac    180
tcagactcat tgaggggccg attcaccgtt tctagagaca cgccagaa ttcggtatat    240 ctccacatga gcagcctgag aggcgaagac acggctctct attactgtgt gagaggctat    300
gatcatagtg attccaactc ggcagcagac ctcctgcatt ggggccgggg caccctggtc    360
accgtctcct cag    373

<210> SEQ ID NO 176
<211> LENGTH: 373
<212> TYPE: DNA
<213> ORGANISM: Artificial Sequence
<220> FEATURE:
<223> OTHER INFORMATION: ANTIBODY

<400> SEQUENCE: 176
gaggtgcagc tggtggagtc tgggggaggc ctggtcaagc cggggggactc tctgacagtc    60 tcctgtgtcg cctctggatt cactttcagc aactatttca tccactgggt ccgacaggct    120
ccagggaagg gactggagtg ggtcgcaacg atcagtggcc gtacgaaata tatgttctac    180
tcagactcat tgaggggccg attcaccgtt tctagagaca cgccgccaa ttcggtatat    240 ctccacatga gcagcctgag aggcgaagac acggctctct attactgtgt gagaggctat    300
gatcatagtg attccaactc ggcagcagac ctcctgcatt ggggccgggg caccctggtc    360

```
accgtctcct cag                                                             373
```

<210> SEQ ID NO 177
<211> LENGTH: 373
<212> TYPE: DNA
<213> ORGANISM: Homo sapiens

<400> SEQUENCE: 177

```
gaggtgcagc tggtggagtc tgggggaggc ctggtcaagc cggggggtc  cctgagactc      60
tcctgtgcag cctctggctt ccccttcagt cgctattcaa tgcactgggt ccgccaggct     120
ccagggaagg ggctggagtg ggtctcatcg atgacgtctc ggactaacca caaatactac     180
gcagactcac tgaagggccg attcctcatc tctcgagaca cgacaggga  ctcactgtac     240
ctggaaatga acagcctggg agtcgaggac acggcgatat atttctgtgc aagaggctat     300
gatactagtg gttccgactc gggagtagac ttccaatact ggggccaggg cacccctggtc    360
accgtctcct cag                                                         373
```

<210> SEQ ID NO 178
<211> LENGTH: 334
<212> TYPE: DNA
<213> ORGANISM: Homo sapiens

<400> SEQUENCE: 178

```
aattttatgc tgactcagcc ccactctgtg tcggagtctc cggggaagac gataaccatc       60
tcctgcaccc gcggcagagg atacattgcc agctactatg tccagtggta ccaacagcgc     120
ccgggcggtg tccccaaaat tgtggtcttt gaggatactc agagaccctc tggggtccct     180
gatcgaatct ctggctccat cgacacctcc accaactctg cctccctcac catctctgga     240
ctgcagactg aagacgaggc tgactactac tgtcagtctt atgatgatgc caatcatgtg     300
atcttcggcg gagggaccaa gctgaccgtc ctag                                  334
```

<210> SEQ ID NO 179
<211> LENGTH: 364
<212> TYPE: DNA
<213> ORGANISM: Homo sapiens

<400> SEQUENCE: 179

```
gaggtgcagc tgttggagtc tgggggaggc ctggtacagc cggggggggcc cctgagactc      60
tcctgtgcag cctctggatt cacctttagc atctacagta tgaactgggt ccgccaggct     120
ccagggaagg ggctggagtg ggtctcaagt attagtggga gtggcgataa tacatactat     180
gcagactccg tgaagggccg gttcaccatc accagagaca gttccaagaa cacactgtat     240
ctgcaaatga acaccctcag agccgaggac acggccgtat attttgtgc  gaaatctgga     300
agaaatatta tatcccctgg atttgactcc tggggccagg aaccctggt  caccgtctcc     360
tcag                                                                    364
```

<210> SEQ ID NO 180
<211> LENGTH: 349
<212> TYPE: DNA
<213> ORGANISM: Homo sapiens

<400> SEQUENCE: 180

```
cagcctgtgc tgactcagcc accttctgca tcagcctccc tgggagcctc ggtcacactc       60
acgtgcaccc tgaacagcga ctatggtgat tataaagtgg actggtacca gcagagacca     120
gggaagggcc cccgatttgt gatgcgagtg ggcactggtg ggattgtggg atccaagggg     180
```

```
gacggcatcc ctgatcgctt ctcagtcttg gggtcaggcc tgaatcggtt cctgaccatt        240
aagaacatcc aggaagagga tgagagtgac tactactgtg gggcagacca tggcagtgcg        300
aacaacttca tttgggtgtt cggcggaggg accaagctga ccgtcctag                    349

<210> SEQ ID NO 181
<211> LENGTH: 366
<212> TYPE: DNA
<213> ORGANISM: Homo sapiens

<400> SEQUENCE: 181
gaggtgcagc tggtggagtc tgggggaggc ttggtcaagc ctggagagtc cctgagactc         60
gcctgtgtag cctctggctt caacttcagt gactactaca tgacgtggat ccgccaggct        120
ccagggaagg gctggagtg gtttcatat attagtaata gtggtagtca cacatactac        180
gcagacgctg tgaagggccg cttcaccgtc tccagggaca atgccaagaa ctcactgtat        240
ctgcaaatga ccagcctgag aggcgaggac acggccatat atttctgtgc gagagatcct        300
tctatcatgc ggggaaccta ctacatggac gtctggggca aagggaccac ggtcaccgtc        360
tcctca                                                                    366

<210> SEQ ID NO 182
<211> LENGTH: 331
<212> TYPE: DNA
<213> ORGANISM: Homo sapiens

<400> SEQUENCE: 182
cagtctgtgc tgactcagcc accctcagcg tctggaaccc ccggccagag ggtcaccatc         60
tcttgttccg gaagcagctc caacatcgga actaaccctg tcagttggta ccagcagttc        120
cccggaatgg cccccaagct cctcatctat tttaacaatc agcggccctc aggggtccct        180
gaacgattct ctggctccaa gtctggcacc ccagcctccc tggccatcgg tggactccag        240
tctgaggatg aggctaacta ttattgtgca tcctgggatg acaccctgaa tggtctggtg        300
ttcggcggag ggaccaagct gaccgtccta g                                       331
```